United States Patent
Ella et al.

(10) Patent No.: US 10,927,147 B2
(45) Date of Patent: Feb. 23, 2021

(54) MURAMYL PEPTIDE DERIVATIVE COMPOUND, SYNTHESIS AND USES THEREOF

(71) Applicants: BHARAT BIOTECH INTERNATIONAL LIMITED, Hyderabad (IN); COUNCIL OF SCIENTIFIC AND INDUSTRIAL RESEARCH, New Delhi (IN)

(72) Inventors: Krishna Murthy Ella, Hyderabad (IN); Ganneru Brunda, Hyderabad (IN); Halmathur Mahabalarao Sampath Kumar, Hyderabad (IN); Miryala Sreekanth, Hyderabad (IN)

(73) Assignees: Bharat Biotech International Limited, Hyderabad (IN); Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 16/060,093

(22) PCT Filed: Dec. 6, 2016

(86) PCT No.: PCT/IN2016/050436
§ 371 (c)(1),
(2) Date: Jun. 7, 2018

(87) PCT Pub. No.: WO2017/098529
PCT Pub. Date: Jun. 15, 2017

(65) Prior Publication Data
US 2018/0371023 A1 Dec. 27, 2018

(30) Foreign Application Priority Data
Dec. 10, 2015 (IN) .......................... 6436/CHE/2015

(51) Int. Cl.
| | |
|---|---|
| *C07K 9/00* | (2006.01) |
| *A61K 39/12* | (2006.01) |
| *A61K 39/00* | (2006.01) |
| *A61K 38/00* | (2006.01) |
| *A61P 33/00* | (2006.01) |
| *A61P 31/12* | (2006.01) |
| *A61P 31/04* | (2006.01) |

(52) U.S. Cl.
CPC .............. *C07K 9/005* (2013.01); *A61K 39/12* (2013.01); *A61K 38/00* (2013.01); *A61K 2039/5555* (2013.01); *A61K 2039/572* (2013.01); *A61K 2039/575* (2013.01); *A61P 31/04* (2018.01); *A61P 31/12* (2018.01); *A61P 33/00* (2018.01); *C12N 2710/00034* (2013.01)

(58) Field of Classification Search
None
See application file for complete search history.

(56) References Cited

U.S. PATENT DOCUMENTS

| | | | |
|---|---|---|---|
| 4,315,913 A | 2/1982 | Durette | |
| 4,409,209 A * | 10/1983 | Baschang | ............... C07K 9/005 514/2.3 |
| 4,427,659 A | 1/1984 | Le Francier | |
| 2018/0360957 A1 | 12/2018 | Ella et al. | |

FOREIGN PATENT DOCUMENTS

| | | |
|---|---|---|
| CA | 2019922 | 12/1990 |
| EP | 0015468 | 9/1980 |
| GB | 1570625 | 7/1980 |
| GB | 1571133 | 7/1980 |
| IN | 6437/CHE/2015 | 7/2018 |
| WO | WO 2017/103944 | 6/2017 |

OTHER PUBLICATIONS

Nerome et al. "Development of a new type of influenza subunit vaccine made by muramyldipeptide-liposome: enhancement of humoral and cellular immune responses" Vaccine 8:503-509. (Year: 1990).*

(Continued)

*Primary Examiner* — Larry D Riggs, II
*Assistant Examiner* — Zachary J Miknis
(74) *Attorney, Agent, or Firm* — Remenick PLLC

(57) ABSTRACT

The invention relates to novel Muramyl Dipeptide (MDP) derivative compound of structural Formula-VIII, a process for synthesis, intermediates used in the synthesis and use thereof.

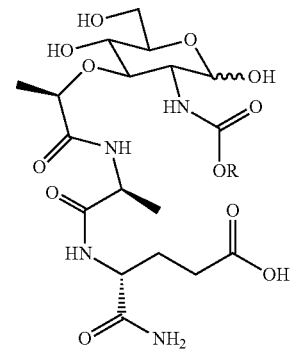

VIII

R = alkyl (both linear and branched), aryl, substituted aryl, alkoxy alkyl

Wherein, R can be both linear and branched alkyl, aryl, substituted aryl and alkoxy alkyl. These compounds possess excellent pharmacological properties, in particular immuno-modulating properties for use as adjuvant in vaccine formulations. These compounds are, particularly useful as adjuvants in vaccines.

7 Claims, 7 Drawing Sheets

(56) References Cited

OTHER PUBLICATIONS

Ogawa et al. "Muramyl dipeptide and its derivatives: peptide adjuvant in immunological disorders and cancer therapy" Curr. Bioact. Compd. 7:180-197. (Year: 2011).*
PubChem "2-[(2S,3R,4R,5S,6R)-3-(Ethoxycarbonylamino)-2,5-dihydroxy-6-(hydroxymethyl)oxan-4-yl]oxypropyl(4R)-5-amino-4-[[(2S,3R)-2-amino-3-methoxybutanoyl]amino]-5-oxopentanoate" (Year: 2012)*
Examination Report for IN Application No. 2018/47011747 dated Jan. 17, 2019.
Examination Report for IN Application No. 2018/47011747 dated Apr. 25, 2018.
Preliminary Examination Report for Application No. PCT/IN2016/050436 dated Apr. 25, 2017.
Search Report for Application No. PCT/IN2016/050436 dated Apr. 25, 2017.
Hong-Zhen Yang et al., "A Novel Immunostimulator, $N^2$-[α-O-Benzyl-N-(acetylmuramyl)-1-alanyl-d-isoglutaminyl]-$N^6$-trans-(m-nitrocinnamoyl)-1-lysine, and Its Adjuvancy on the Hepatitis B Surface Antigen" Journal of Medicinal Chemistry, vol. 48 (16): 5112-5122, 2005.
Supplemental Search Report for EP Application No. 16 87 2570 dated May 28, 2019.

* cited by examiner

MURAMYL PEPTIDE DERIVATIVE COMPOUND, SYNTHESIS AND USES THEREOF

CROSS REFERENCE

This PCT application claims priority from Indian Provisional Patent Application No. 6436/CHE/2015 filed in India dated Dec. 10, 2015.

FIELD OF THE INVENTION

The invention relates to novel Muramyl Dipeptide (MDP) derivative compounds of structural formula VIII

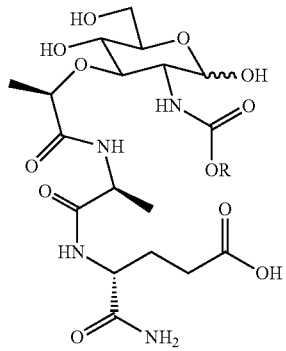

(VIII)

R = alkyl (both linear and branched),
aryl, substituted aryl, alkoxy alkyl

The invention also relates to process for preparation of these novel compounds and novel intermediates for preparation of these novel compounds. The novel compounds of the invention have high potential of immuno-modulating properties for use as adjuvants in vaccine formulations. The invention also relates to use of these novel compounds as adjuvants with vaccine antigens and in preparation of vaccine formulations.

BACKGROUND OF THE INVENTION

Muramyl dipeptide (MDP, N-acetylmuramyl-L-alanyl-D-isoglutamine) is a synthetic immunoreactive peptide consisting of N-acetyl muramic acid attached to a short amino acid chain of L-Ala-D-isoGln. It was first identified in bacterial cell wall peptidoglycan as an active component in Freund's Complete Adjuvant (FCA). In 1974, MDP was discovered to be the minimal structure required for the efficacy of FCA, one of the most potent and widely used adjuvants in animal experimental models. Muramyl dipeptides are well known for their immunomodulatory properties. Muramyl dipeptides are the smallest, biologically active components of bacterial cell walls. Muramyl dipeptide derivatives have been proved to show significant immunomodulatory properties, via one of the PRRs (Pattern Recognition Receptors), nucleotide-binding oligomerization domain 2 (NOD2) receptor (Girardin S. et al., 2003. *J Biol Chem.* 278(11): 8869-72; F. Coulombe et al., 2012 *PloS ONE,* 7 (5): *Article ID e*36734). Muramyldipeptides activate macrophages and other cells of the immune system to kill cancer cells (I. Jakopin, 2013. *Current Medicinal Chemistry,* 20 (16): 2068-2079; Ogawa et. al., 2011. *Curr Bioact Compd.* 7(3): 180-197), however, it is also reported to be pyrogenic in nature. In order to reduce its pyrogenic effect, till date a series of MDP derivatives have been designed, synthesized and tested with the aim of increasing specific functions, while suppressing pyrogenicity. There are many reported inventions or publications related to synthesis of Muramyl dipeptide and its derivatives (Namba et al., 1997. *Vaccine,* 15(4): 405-13; WO1996001645; U.S. Pat. Nos. 4,395,399; 7,173,107 B2).

N-glycolyl muramyl dipeptide, GMDP (N-glycolyl glucosaminyl-N-acetylmuramyl-L-alanyl-D-isoglutamine) is one of the example of Muramyl dipeptide derivative, which was originally developed in the 1970s at the Shemyakin Institute for Bio-organic Chemistry, Moscow. GMDP has been shown to stimulate both innate and adaptive immune responses. GMDP also activates macrophages and release cytokines and colony stimulating factors (CSFs), which in turn stimulate the differentiation of hemopoietic cells to clear infections (*Australasian Biotechnology*, Volume 6 Number 4, July/August 1996, pp. 223-229). GMDP have been, shown to have higher immunoadjuvant activity and less pyrogenic effect, compared to MDP. Hence, several other N-acyl derivatives of MDP are more immuno-therapeutics over MDP (Andronova T. M., et al., 1991. *Review. Immunology* 4, 1). Hence, this molecule is been widely used in immuno-therapeutic approaches, especially to treat chronic infections, autoimmune diseases and cancer (L. I. Rostovtseva et al., 1981. *Russian Journal of Bioorganic Chemistry,* 7 (12): 1843-1858).

MDP-based compound Likopid™ is the first immunotherapeutic of the muramylglycopeptide type introduced to the clinical practice. Likopid™ was developed and registered by a Russian company Peptek as an immunotherapeutic with broad applicability, e.g. immunostimulation and prevention of infections complicating post-traumatic, post-operative, post-chemotherapeutic and post-radiotherapeutic patienthood. Other areas are treatment of infectious diseases, as tuberculosis, human cervical papilomavirus, ophthalmic herpetic infections, psoriasis and treatment of ulcerous and inflammation processes (WO2007045192).

Below shown structure of general Formula-X represents chemical structure of compound MDP.

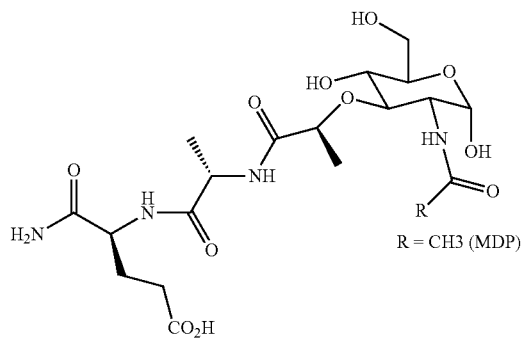

Formula-X

R = CH3 (MDP)

Structural representation of MDP

There are many inventions related to Muramyl peptide compounds and its derivatives. Although, there use as therapeutic agents is known, use of MDP derivatives as adjuvants in vaccine formulations has not been repored or found at all till present.

WO1996001645 A1 relates to the use of Muramyl peptide compounds, particularly N-acetyl-D-glucosaminyl-(β1-4)-N-acetylmuramyl-L-alanyl-D-isoglutamine (MDP), for the treatment of inflammatory dermatological conditions such as psoriasis and in the treatment of immune-related diseases of the skin and mucous membranes.

U.S. Pat. No. 7,173,107B2 discloses glycopeptides and preparation thereof which is stereo-specific synthesis of a glycopeptide using a triply orthogonal protection scheme is described, in particular, the synthesis of N-acetylglucosaminyl-β-[1,4]-N-acetylmuramyl monopeptide and derivatives thereof. The glycopeptide is useful for the preparation of MDP and related compounds having a glucosaminyl-β-[1, 4]-N-acetylmuramic acid disaccharide core.

WO2007045192 relates to glucosaminylmuramic acid (2-amino-2-deoxy-β-D-gluco-pyranosyl-(1→4)-N-acetylmuramic acid) derivatives, method of their synthesis, and their use for the synthesis of glucosaminylmuramylglycopeptides, i.e. disaccharide analogues of muramylglycopeptides. U.S. Pat. No. 4,395,399 disclose different glycopeptides and their preparations.

However, despite improvements seen in several newly developed MDP derivatives, yet there is a continuous need for compounds with further reduced side-effects and increased adjuvant activity for the purpose of either therapeutic or prophylactic use in vaccine formulations. Hence it is critical to focus on the balance between efficacy and side effects, while designing or synthesizing new compounds. There is a need to develop more effective and improved MDP derivatives, which would reduce the side effects associated with known MDP derivatives.

OBJECTS OF THE INVENTION

The primary object of the invention is to provide novel Muramyl Dipeptide derivative compounds.

Another object of the invention is to provide a process for preparation of novel Muramyl Dipeptide derivative compounds.

Another object of the invention is to provide novel intermediate compounds for the synthesis of novel Muramyl Dipeptide derivative compounds.

A further object of the invention is to provide safe use of novel Muramyl Dipeptide derivative compounds as adjuvant for pharmaceutical preparations and vaccine formulations.

Still a further object is to provide a vaccine formulation comprising novel Muramyl Dipeptide derivative compound.

SUMMARY OF THE INVENTION

Accordingly, the invention discloses novel MDP derivative compounds of structural formula VIII with reduced pyrogenicity, while maintaining a considerable effective functionality as vaccine adjuvants.

In one aspect, the invention provides novel muramyl dipeptide derivative compounds as shown below in general Formula-VIII:

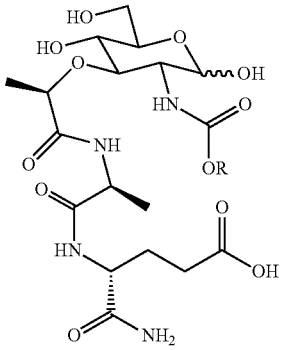

General Structural Formula-VIII

R = alkyl (both linear and branched), aryl, substituted aryl, alkoxy alkyl

In one preferred embodiment when R is ethyl (C2H5) the compound of Formula-VIII is (4R)-5-amino-4-((2S)-2-((2R)-2-(((3R,4R,5S,6R)-3-((alkoxycarbonyl) amino)-2,5-dihydroxy-6-(hydroxymethyl) tetrahydro-2H-pyran-4-yl) oxy) propanamido) propanamido)-5-oxopentanoic acid as shown in below structure:

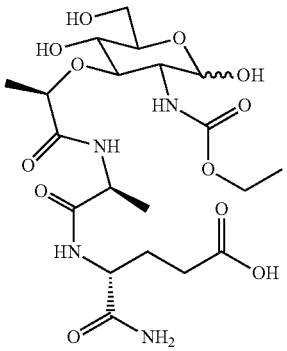

When R is ethyl

In another aspect, the invention provides a process for the synthesis of the novel Muramyl Dipeptide derivative compounds of general formula-VIII comprising the steps as shown in Scheme A and Scheme B.

In further aspects of the invention, the novel Muramyl Dipeptide derivative of the present invention is evaluated for its activity. The safety of the novel Muramyl Dipeptide derivative of the present invention is established through cytotoxicity and pyrogenecity assays.

In another aspect, the invention provides use of novel muramyldipeptide derivative (4R)-5-amino-4-((2S)-2-((2R)-2-(((3R,4R,5S,6R)-3-((ethoxycarbonyl)amino)-2,5-dihydroxy-6-(hydroxymethyl) tetrahydro-2H-pyran-4-yl) oxy) propanamido) propanamido)-5-oxopentanoic acid as an adjuvant to be used in the pharmaceutical preparations and vaccine formulations.

Additionally, in further embodiments of the invention, the in-vivo immunogenecity of the novel Muramyl Dipeptide derivative of the present invention is shown to effectuate at least 4-fold increase in antibody titers when used as adjuvant with various vaccine antigens, thereby capable of generating both humoral and cell-mediated immune response.

In general embodiment, the invention provides a Muramyl Dipeptide derivative compound-VIII

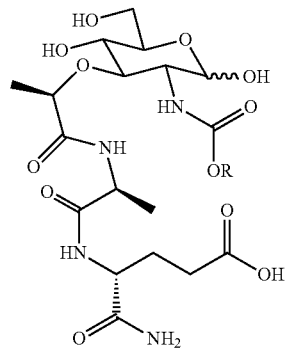

(VIII)

R = alkyl (both linear and branched), aryl, substituted aryl, alkoxy alkyl wherein, R is alkyl (both linear and branched), aryl, substituted aryl or alkoxy alkyl.

In one embodiment, the compound is (4R)-5-amino-4-((2S)-2-((2R)-2-(((3R,4R,5S,6R)-3-((ethoxycarbonyl)amino)-2,5-dihydroxy-6-(hydroxymethyl) tetrahydro-2H-pyran-4-yl)oxy) propanamido) propanamido)-5-oxopentanoic acid (MDP-ET) as shown in below structure.

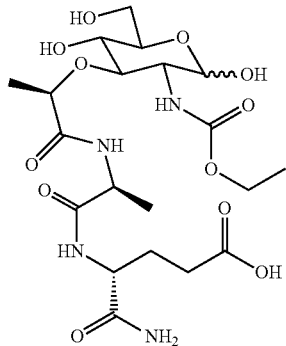 [SMILES: CCOC(=O)NC1C(O)OC(CO)C(O)C1O[C@H](C)C(=O)N[C@@H](C)C(=O)N[C@H](CCC(=O)O)C(N)=O]

(MDP-ET)

The compound MDP-ET is characterized by IR (n in cm$^{-1}$): 3273, 2936, 1653, 1552, 1417, 1253, 1026. The compound MDP-ET is further characterized by 1H-NMR (300 MHz, DMSO-d$_6$): δ 4.66 (d, J=6.421, 1H), 4.25 (m, 1H), 3.96 (m, 3H), 3.37 (q, J=6.987, 3H), 3.19-3.16 (m, 2H), 2.17 (m, 2H), 1.99 (m, 1H), 1.24 (m, 4H), 1.15 (d, J=6.409, 3H), 1.08 (t, J=6.987, 3H).

In another embodiment, the invention provides a process for preparation of a Muramyl Dipeptide derivative compound of Formula-VIII

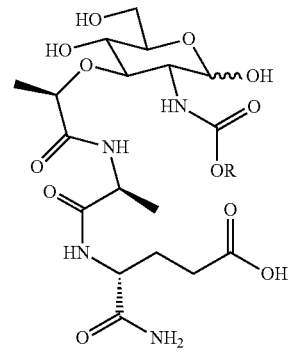

(VIII)

R = alkyl (both linear and branched), aryl, substituted aryl, alkoxy alkyl comprising the steps of:
a. anomeric benzylation of a compound of Formula-I to obtain a compound of Formula-II;

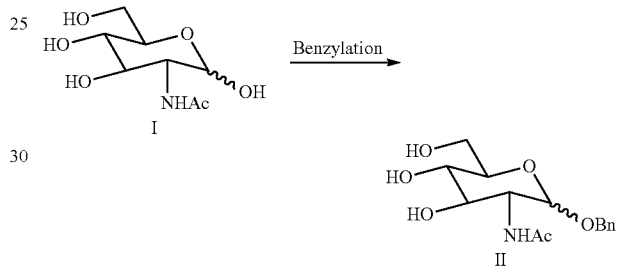

b. benzylidene protection of the compound of Formula-II to obtain a compound of Formula-III;

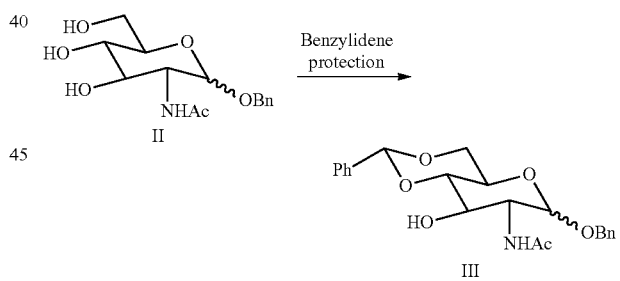

c. deacylating the compound of Formula-III to obtain a compound of Formula-IV;

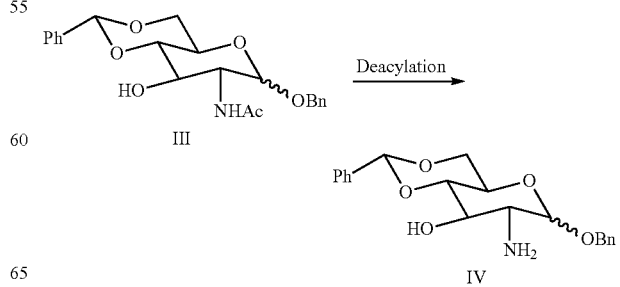

d. re-acylating the compound of Formula-IV with a suitable acylating agent in presence of a solvent, to obtain a compound of Formula-V;

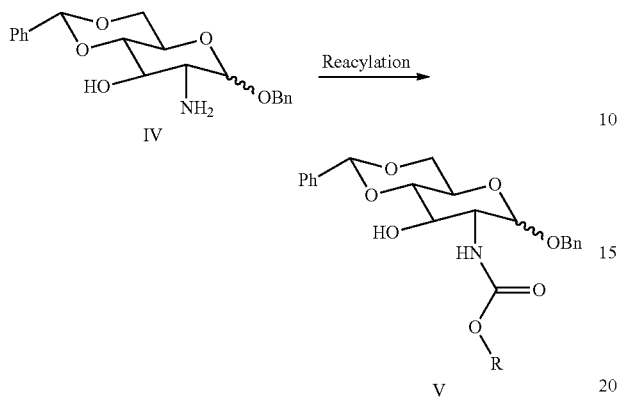

e. O-alkylating the compound of Formula-V by treating with L-2-chloropropanoic acid in presence of a solvent to obtain a compound of Formula-VI;

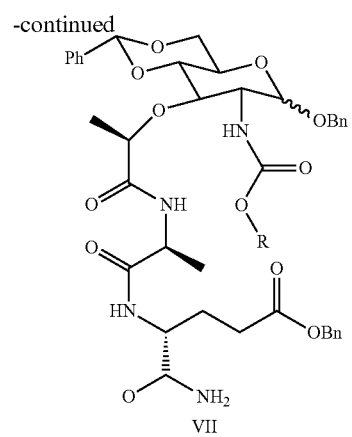

f. coupling a peptide by treating the compound of Formula VI with L-alanyl-D-isoglutamine benzyl ester trifluoroacetate in a solvent to obtain a compound of Formula-VII;

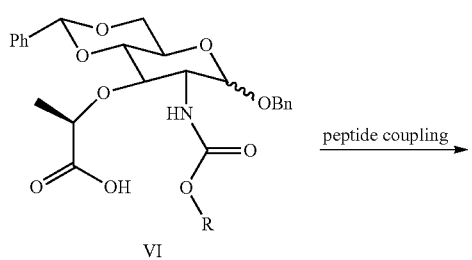

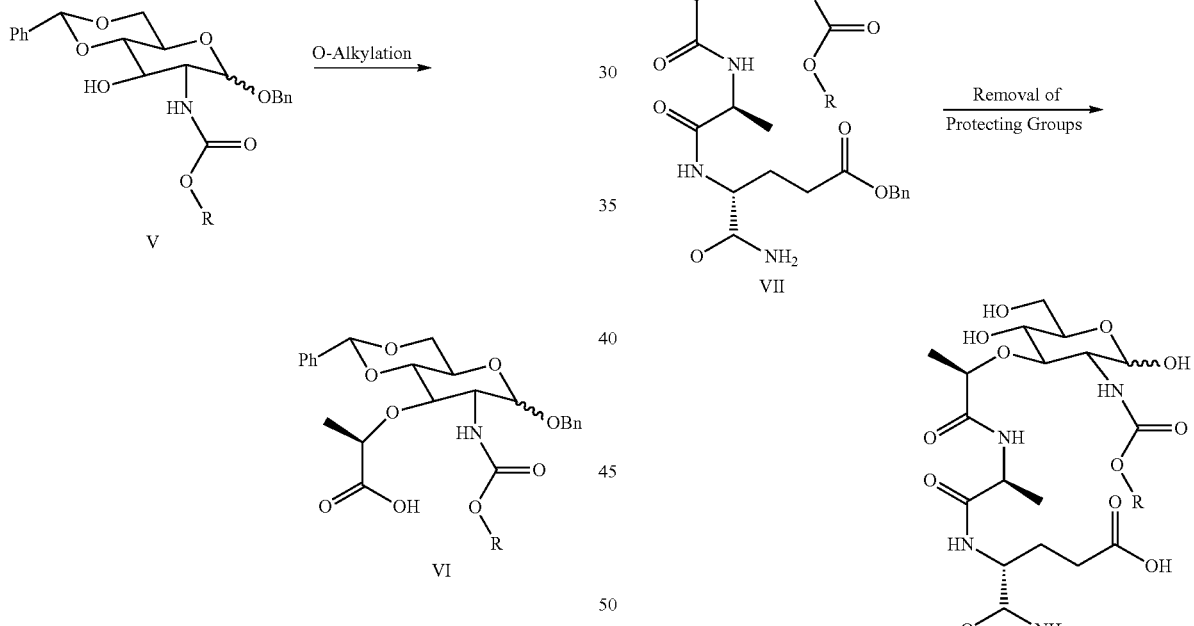

g. deprotecting the compound of Formula-VII to obtain the desired compound as represented by Formula-VIII;

STRUCTURAL FORMULA-VIII ## wherein, R in above compounds is alkyl (both linear and branched), aryl, substituted aryl, alkoxy aryl.

The acylating agent in step (d) may be selected from alkyl chlofomate and alkoxy alkyl chloroformate.

In one embodiment, acylating agent is preferably ethyl chloroformate.

The solvent in step (d) may be selected from dry pyridine, di-isopropyl ethyl amine, tri-ethylamine, and N, N, dimethyl amino pyridine (DMAP) or mixture thereof. And the solvent in step (e) is dry dioxane.

The solvent in step (f) may be selected from trifluoroacetic acid (TFA) and tetrahydrofuran (THF) or mixture thereof.

The coupling in step (f) is carried out in presence of 1-Ethyl-3-(-3-dimethyl amino propyl) carbodiimide (EDCI) and Hydroxybenzotriazole (HOBt).

The deprotection in step (g) is carried out with glacial acetic acid.

In one embodiment, the invention provides a compound of Formula V:

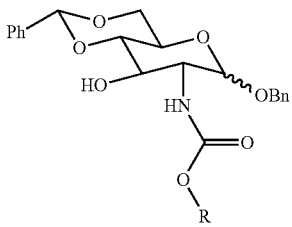

V wherein R is selected from any alkyl (both linear and branched), aryl, substituted aryl and alkoxy alkyl group.

In another embodiment, the invention provides a compound of Formula VI:

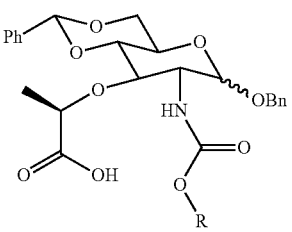

VI wherein R is selected from any alkyl (both linear and branched), aryl, substituted aryl and alkoxy alkyl group.

In a further embodiment, the invention provides a compound of Formula VII:

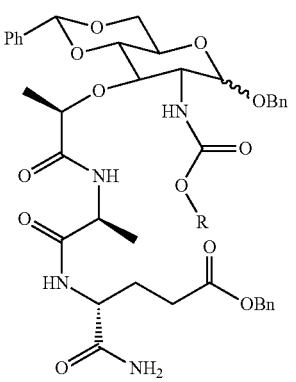

VII wherein R is selected from any alkyl (both linear and branched), aryl, substituted aryl and alkoxy alkyl group.

In another embodiment, the invention provides a compound ethyl ((4aR,6S,7R,8R,8aS)-6-(benzyloxy)-8-hydroxy-2-phenylhexahydropyrano[3,2-d][1,3]dioxin-7-yl) carbamate characterized by $^1$HNMR(CDCl$_3$): 7.2-7.5 (m, 10H), 5.6 (s, 1H), 5.4 (s, 1H), 4.7 (d, 1H), 4.6 (d, 1H), 4.4 (d, 1H), 4.2 (d, 1H), 3.7-3.9 (m, 4H), 1.4 (t, 3H), ESI MS: 430 (M$^+$).

In another embodiment, the invention provides a compound (2R)-2-(((4aR,6S,7R,8R,8aS)-6-(benzyloxy)-7-((ethoxycarbonyl) amino)-2-phenyl hexahydropyrano[3,2-d][1,3]dioxin-8-yl) oxy) propanoic acid characterized by $^1$HNMR(CDCl$_3$): 7.2-7.6 (m, 10H), 5.6 (s, 1H), 5.1 (s, 1H), 4.9-3.94 (m, 7H), 3.8-3.4 (m, 4H), 1.4 (d, 2H), 1.3 (t, 3H); ESI MS: 502 (M$^+$).

In another embodiment, the invention provides a compound (4R)-benzyl 5-amino-4-((2S)-2-((2R)-2-(((4aR,6S,7R,8R,8aS)-6-(benzyloxy)-7-((ethoxycarbonyl)amino)-2-phenylhexahydropyrano[3,2-d][1,3]dioxin-8-yl)oxy) propanamido)propanamido)-5-oxopentanoate characterized by $^1$HNMR(CDCl$_3$): 7.5 (m, 2H), 7.2-7.4 (m, 11H), 6.9 (d, 2H) 5.5 (s, 1H), 5.2 (d, 1H), 4.9 (d, 1H), 4.7 (d, 1H), 4.5 (d, 1H), 4.4 (t, 1H), 4.2 (m 2H), 4.0 (m, 2H) 3.75 (m, 3H), 3.5 (m, H), 2.5 (s, 1H), 1.5-1.7 (m, 7H) 1.4 (t, 3H), 1.2 (t, 3H) ESI MS: 792 (M$^+$+1).

In another embodiment, the invention provides a process for preparation of (4R)-5-amino-4-((2S)-2-((2R)-2-(((3R,4R,5S,6R)-3-((ethoxycarbonyl)amino)-2,5-dihydroxy-6-(hydroxymethyl)tetrahydro-2H-pyran-4-yl) oxy) propanamido) propanamido)-5-oxopentanoic acid (MDP-ET) comprising the steps of:

(a) anomeric benzylation of N-acetyl D-Glucosamine (I) to obtain Benzyl 2-acetamido-2-deoxy-α-D-glucopyranoside (II);

(b) benzylidene protection of Benzyl 2-acetamido-2-deoxy-α-D-glucopyranoside (II) to obtain benzyl 2-acetamido-4,6-O-benzylidene-2-deoxy-D-glucopyranoside (III);

(c) deacylation of benzyl 2-acetamido-4,6-O-benzylidene-2-deoxy-D-glucopyranoside (III) to obtain benzyl-2-amino-4,6-O-benzylidene-2-deoxy-α-D-mannopyranoside (IV);

(d) re-acylation with an organic acylating agent ethyl chloroformate in presence of a solvent dry pyridine of benzyl-2-amino-4,6-O-benzylidene-2-deoxy-a-D-mannopyranoside (IV) to obtain ethyl ((4aR,6S,7R,8R,8aS)-6-(benzyloxy)-8-hydroxy-2-phenylhexahydropyrano[3,2-d][1,3]dioxin-7-yl) carbamate (V);

(e) o-alkylation of ethyl ((4aR,6S,7R,8R,8aS)-6-(benzyloxy)-8-hydroxy-2-phenylhexahydropyrano[3,2-d][1,3]dioxin-7-yl)carbamate (V) in presence of a solvent dry dioxane to obtain (2R)-2-(((4aR,6S,7R,8R,8aS)-6-(benzyloxy)-7-((ethoxycarbonyl)amino)-2-phenyl-hexahydropyrano[3,2-d][1,3]dioxin-8-yl)oxy)propanoic acid (VI);

f. peptide coupling of (2R)-2-(((4aR,6S,7R,8R,8aS)-6-(benzyloxy)-7-((ethoxycarbonyl)amino)-2-phenyl-hexahydropyrano[3,2-d][1,3]dioxin-8-yl)oxy)propanoic acid (VI) with L-alanyl-D-isoglutamine benzyl ester trifluoroacetate to obtain (4R)-benzyl 5-amino-4-((2S)-2-((2R)-2-(((4aR,6S,7R,8R,8aS)-6-(benzyloxy)-7-((ethoxycarbonyl)amino)-2-phenylhexahydropyrano[3,2-d][1,3]dioxin-8-yl)oxy)propanamido) propanamido)-5-oxopentanoate (VII);

(g) deprotecting (4R)-benzyl 5-amino-4-((2S)-2-((2R)-2-(((4aR,6S,7R,8R,8aS)-6-(benzyloxy)-7-((ethoxycarbonyl)amino)-2-phenylhexahydropyrano[3,2-d][1,3]dioxin-8-yl)oxy)propanamido)propanamido)-5-oxopentanoate (VII) in presence of glacial acetic acid to obtain (4R)-5-amino-4-((2S)-2-((2R)-2-(((3R,4R,5S,6R)-3-((ethoxycarbonyl)amino)-2,5-dihydroxy-6-(hydroxymethyl)tetrahydro-2H-pyran-4-yl)oxy)propanamido)propanamido)-5-oxopentanoic acid.

In another embodiment, the invention provides the use of the compound VIII or MDP-ET as an adjuvant in vaccine formulation with an antigen wherein the antigen may be selected from a live attenuated vaccine antigen, inactivated vaccine antigen, subunit vaccine antigen, a conjugate vaccine antigen, and recombinant vaccine antigen or any combinations thereof.

In another embodiment, the invention provides a vaccine formulation comprising compound of Formula VIII as an adjuvant.

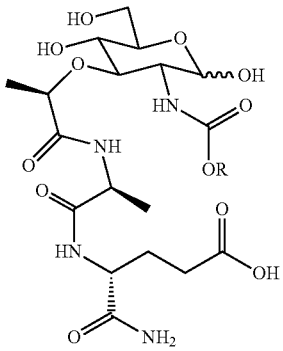

(VIII)

R = alkyl (both linear and branched),
aryl, substituted aryl, alkoxy alkyl

In another embodiment, the invention provides a vaccine formulation comprising the compound (4R)-5-amino-4-((2S)-2-((2R)-2-(((3R,4R,5S,6R)-3-((ethoxycarbonyl)amino)-2,5-dihydroxy-6-(hydroxymethyl) tetrahydro-2H-pyran-4-yl)oxy) propanamido) propanamido)-5-oxopentanoic acid (MDP-ET) as shown in below structure, as an adjuvant

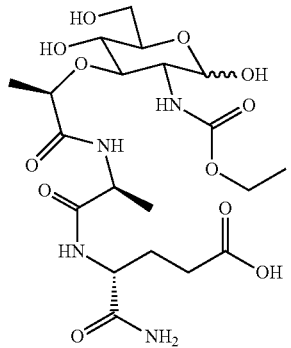

Wherein, vaccine formulation may be selected from a bacterial vaccine, a viral vaccine or any potential infectious pathogens against mammals.

DETAILED DESCRIPTION OF THE INVENTION

Figure 1:
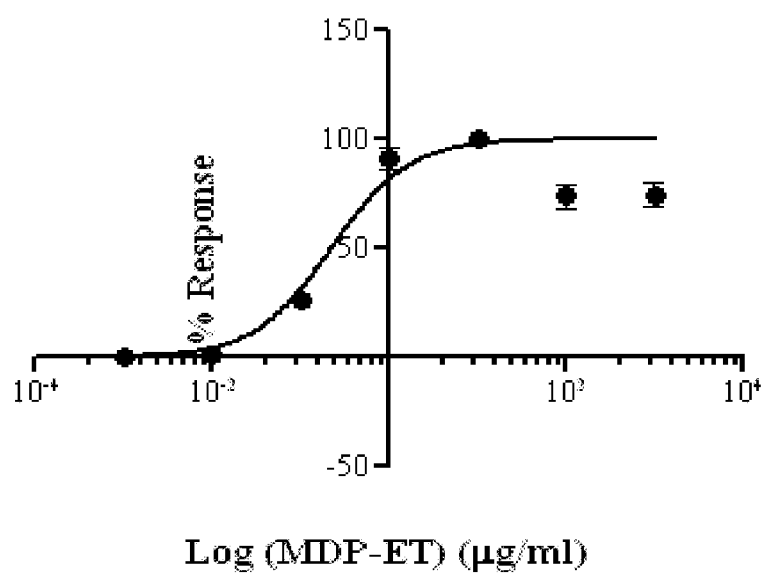
FIG. 1: the figure represents dose response curve of MDP-ET. X-axis represents concentration in log scale and Y-axis represents % response. Y-axis values were normalized by taking smallest value or low absorbance as 0% and largest value or high absorbance as 100%. This graph indicates $EC_{50}$ as 0.22 µg/ml, the concentration at which adjuvant is showing half maximal response. Each data set point is represented as a Mean±SD, which was obtained from three independent experiments done in duplicates.

The present invention provides novel Muramyl Dipeptide (MDP) derivative compounds of general Formula-VIII, process for synthesis, novel intermediate compounds used in the synthesis and uses thereof as adjuvants in the immunogenic preparations.

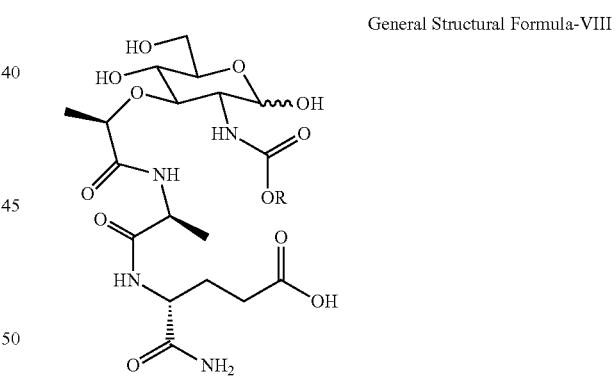

General Structural Formula-VIII

R = alkyl (both linear and branched),
aryl, substituted aryl, alkoxy alkyl

The alkyl is linear or branched of any suitable carbon length. In one embodiment the alkyl is linear alkyl. Non-limiting exemplary linear alkyl may be selected from methyl, ethyl, propyl, butyl etc. In one embodiment the alkyl is ethyl (R=ethyl).

Non-limiting exemplary aryl group may be selected from phenyl, naphthyl, thienyl, indolyl, etc. The aryl group can be a substituted aryl.

In one embodiment R in Formula-VIII is alkyl, wherein alkyl is as defined above. When R is alkyl (R=alkyl), the novel muramyl dipeptide derivative compound of Formula-VIII of the invention is (4R)-5-amino-4-((2S)-2-((2R)-2-

(((3R,4R,5S,6R)-3-((alkoxycarbonyl) amino)-2,5-dihydroxy-6-(hydroxymethyl) tetrahydro-2H-pyran-4-yl)oxy) propanamido) propanamido)-5-oxopentanoic acid.

In one embodiment R in Formula-VIII is ethyl (R=Ethyl). When R is ethyl, the novel muramyl dipeptide derivative compound of the invention is (4R)-5-amino-4-((2S)-2-((2R)-2-(((3R,4R,5S,6R)-3-((ethoxycarbonyl) amino)-2,5-dihydroxy-6-(hydroxymethyl) tetrahydro-2H-pyran-4-yl)oxy) propanamido) propanamido)-5-oxopentanoic acid as shown below in Structural Formula-VIII (when R is ethyl):

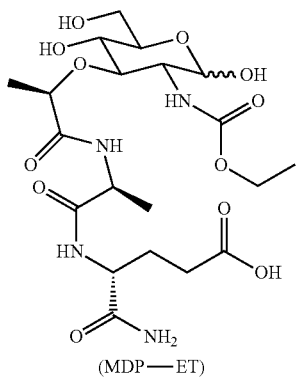

(MDP—ET)

[Formula-VIII, when R = Ethyl]

The novel muramyl dipeptide derivative compounds of general Formula-VIII (when R is as defined above) including the alkoxycarbonyl derivative (when R is alkyl) and (4R)-5-amino-4-((2S)-2-((2R)-2-(((3R,4R,5S,6R)-3-((ethoxycarbonyl) amino)-2,5-dihydroxy-6-(hydroxymethyl) tetrahydro-2H-pyran-4-yl)oxy) propanamido) propanamido)-5-oxopentanoic acid of Formula-VIII (when R is ethyl) are synthesized sequentially by below shown reaction steps mentioned separately in Scheme A and Scheme-B.

The novel MDP derivative compounds having the general structural Formula VIII including Formula-VIII when R is alkyl (alkoxycarbonyl derivative) or R is ethyl (MDP-ET) as shown above are synthesized as per the process depicted in Scheme B. Additionally, the starting compound, L-alanyl-D-isoglutamine benzyl ester which was used in the synthesis of the novel MDP derivative compounds having the general structural Formula VIII including Formula-VIII when R is alkyl or ethyl (MDP-ET) as shown below in Scheme B, was synthesized according to the below shown Scheme A (Synthesis of starting dieptide). Thereafter, novel MDP derivative compounds of Formula-VIII including MDP-ET are obtained according to step wise reactions as mentioned in the Scheme B.

SCHEME-B for the synthesis of Muramyl Peptide Derivative of structural Formula-VIII is depicted below:

SCHEME-B

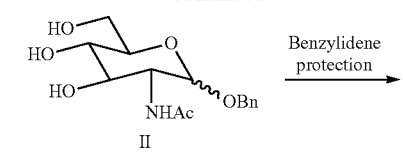

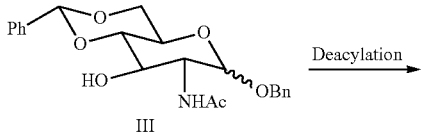

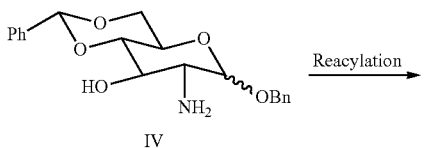

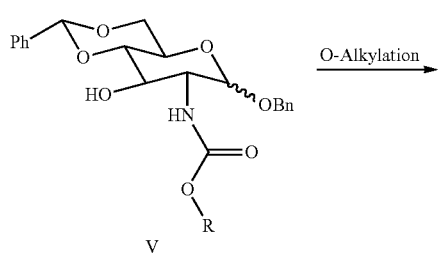

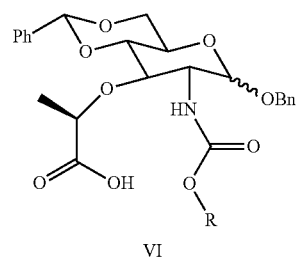

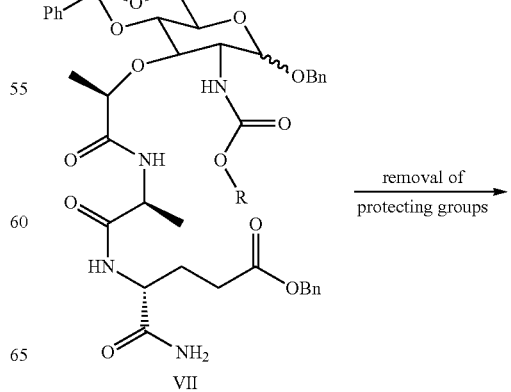

-continued

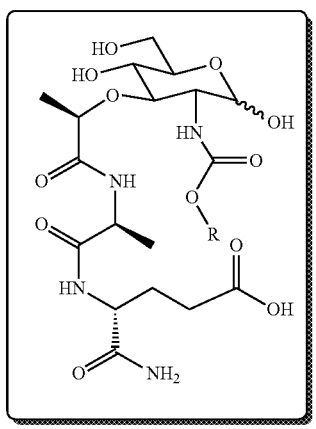

Structural Formula-VIII
(MDP-ET)

Wherein R = alkyl (both linear and branched), aryl, substituted aryl and alkoxy alkyl.
When R = Ethyl, Formula-VIII is MDP-ET SCHEME-A for the synthesis of the L-alanyl-D-isoglutamine benzyl ester of novel muramyl dipeptide compound is depicted below:

SCHEME-A
SCHEME FOR THE SYNTHESIS OF DIPEPTIDE

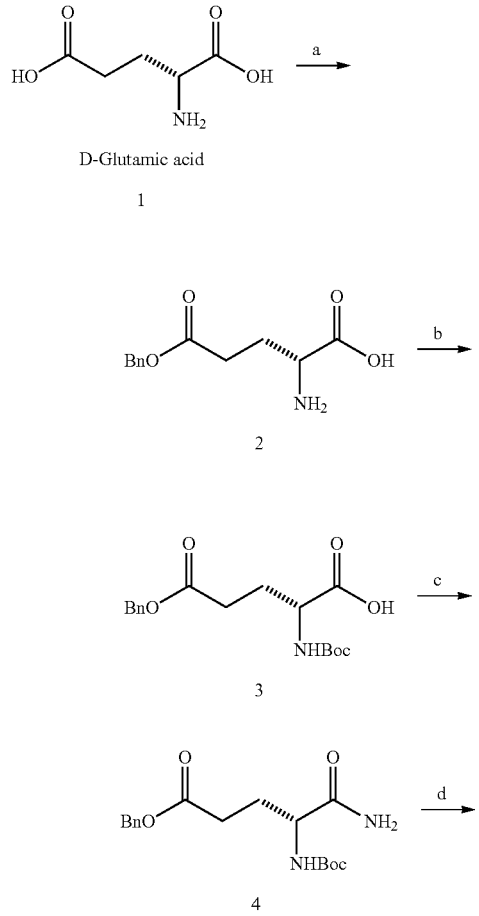

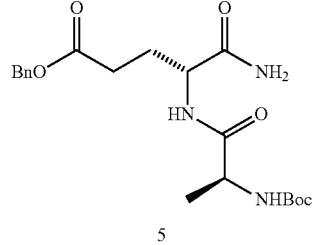

Reagents and conditions: a) BnOH, BF$_3$·Et$_2$O, rt, 15 h, 94%;
b) NaHCO$_3$, (Boc)$_2$O, THF, H$_2$O, rt, 12 h, 96%;
c) ClCOOEt, Et$_3$N, NH$_4$OH, THF, 0° C. to -15° C., 1.5 h, 90%;
d) i. TFA:CH$_2$Cl$_2$, then, ii. Boc-Ala, EDCl, HOBt, DIPEA, THF, 0° C. to rt, 6 h, 87%

In another aspect the present invention provides novel intermediate compounds of general Formula V, VI and VII as shown above in Scheme-B, which are used in the synthesis of novel MDP derivative compounds of above general Formula-VIII.

In one embodiment the invention provides an intermediate compound with structural formula V as represented below:

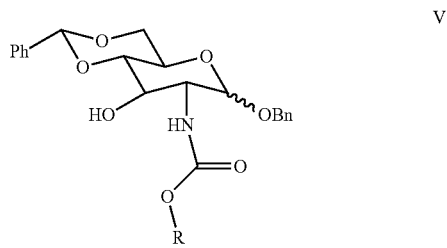

In one embodiment the invention provides an intermediate compound with structural formula VI as represented below:

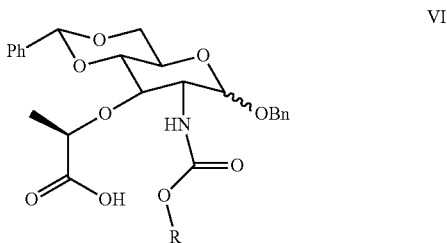

In one embodiment the invention provides an intermediate compound with structural formula VII as represented below:

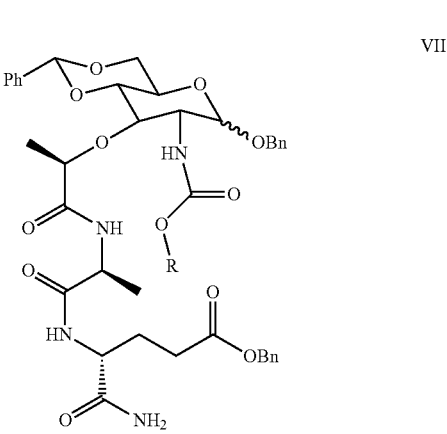

R in any of general Formula-V, Formula-VI and Formula-VII is selected from any alkyl (both linear and branched), aryl, substituted aryl and alkoxy alkyl group as defined above.

In one embodiment R in above intermediate compounds of general Formula-V, Formula-VI and Formula-VII is alkyl.

In one embodiment the intermediate compound of:
Formula-V is ethyl ((4aR,6S,7R,8R,8aS)-6-(benzyloxy)-8-hydroxy-2-phenyl hexahydropyrano[3,2-d][1,3]dioxin-7-yl) carbamate;
Formula-VI is (2R)-2-(((4aR,6S,7R,8R,8aS)-6-(benzyloxy)-7-((ethoxycarbonyl) amino)-2-phenyl hexahydropyrano[3,2-d][1,3]dioxin-8-yl)oxy) propanoic acid; and
Formula-VII is (4R)-benzyl 5-amino-4-((2S)-2-((2R)-2-(((4aR,6S,7R, 8R,8aS)-6-(benzyloxy)-7-((ethoxycarbonyl) amino)-2-phenylhexahydropyrano[3,2-d][1,3] dioxin-8-yl)oxy) propanamido) propanamido)-5-oxopentanoate.

In another aspect the invention provides a process for synthesis of novel MDP derivative compound of Formula-VIII involving the reaction steps as depicted in above Scheme-A (synthesis of the L-alanyl-D-isoglutamine benzyl ester) and Scheme-B (synthesis of novel MDP derivative of Formula-VIII).

Compound 2 is synthesized by providing a mixture of D-Glutamic acid [Compound 1] and anhydrous sodium sulphate ($Na_2SO_4$) suspended in benzyl alcohol and Boron triflouride ($BF_3$). To this mixture, Diethyl Ether is added and the suspension is stirred at room temperature (RT) followed by diluting with absolute THF and filtering with the aid of charcoal. Further treatment with triethyl amine, concentrating, precipitating followed by washing it provides (R)-2-amino-5-(benzyloxy)-5-oxopentanoic acid [Compound 2].

Compound 3 is prepared by providing a solution of the compound 2, adding with Di-tert-butyl dicarbonate ($Boc_2O$) in dixoane and water at low temperature such as 0° C. and stirring overnight. Then solvent is removed under reduced pressure and the residue is diluted with water, basified with Sodium Carbonate ($Na_2CO_3$) and washed with Ethyl Acetate (EtOAc), adjusted to pH 2-3 with aqueous HCl solution and extracted with EtOAc followed by further processing to get (R)-5-(benzyloxy)-2-(tert-butoxycarbonyl)-5-oxopentanoic acid [Compound 3].

Compound 4 is synthesized by providing Compound 3 in Tetrahydrofuran (THF), adding ethyl chloroformate and triethylamine at low temperature such as 0° C. The reaction mixture is stirred at low temperature, and then cooled to low temperature (such as −15° C.) followed by addition of methanolic solution of ammonia and further cooling to minus temperature and is added with ethyl acetate. After washing the organic phase with water followed by washing with brine solution, drying, removing solvent in vacuum and purification (R)-benzyl 5-amino-4-((tert-butoxy carbonyl) amino)-5-oxopentanoate [Compound 4] is obtained.

t-Butoxy carbonyl-D-isoglutamine benzyl ester [Compound 4] is dissolved in cold trifluoroacetic acid and the resultant solution is stirred at RT and then Trifluoroacetic acid is removed and the residue is triturated with Diethyl Ether ($Et_2O$) to obtain oily D-isoglutamine benzyl ester trifluoroacetate. Separately, to t-butoxycarbonyl-L-alanine in dry THF, 1-Ethyl-3-(3-dimethylaminopropyl) carbodiimide (EDCI) and Hydroxy benzotriazole (HOBt) are added and stirred at RT. To this solution, D-isoglutamine benzyl ester trifluoroacetate (dissolved in THF) is added followed by N,N-Diisopropylethylamine (DIPEA). After stirring and concentrating the residue is extracted with EtOAc, washed and dried to obtain a residue. After further washing and recrystallization it provides (R)-benzyl 5-amino-4-((S)-2-((tert-butoxy carbonyl) amino) propanamido)-5-oxopentanoate [Compound 5].

In another aspect the invention provides a process for a process for preparation of a muramyl dipeptide derivative compound of Formula-VIII

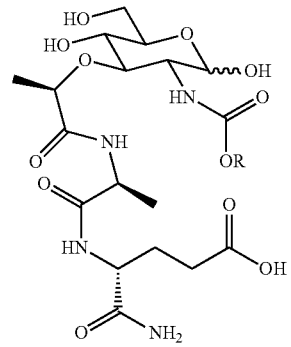

Formula-VIII

R = alkyl (both linear and branched), aryl, substituted aryl, alkoxy alkyl wherein R is as defined in above paragraphs.

The process comprises following steps (a) to (g):

Step-a: Anomeric Benzylation of N-acetyl D-Glucosamine (I):

Step (a) involves anomeric benzylation of a compound of Formula-I to obtain a compound of Formula-II as schematically presented below:

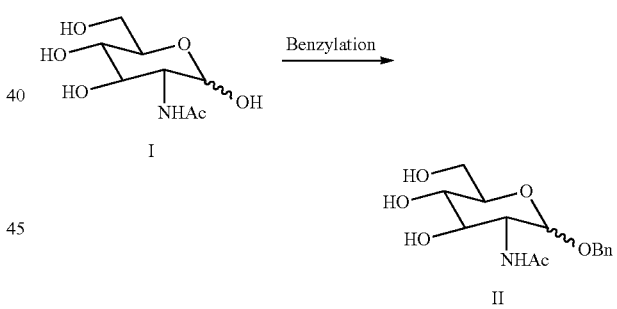

Anomeric benzylation takes place by treating the compound of Formula-I with benzyl alcohol with stirring. The reaction may be carried out in presence of an ion exchange resin such as Amberlite or other resin. The reaction can be performed at temperature about 70 to 90° C. Preferably in one embodiment stirring is done at 80° C. and evaporation is done at 90° C.

The residue after filtration of the mixture is taken up in hot alcoholic solvents and filtered. Preferably the alcoholic solvent used is isopropanol. Further crystallization affords white crystalline solid. The solid obtained may be washed with alcoholic solvent such as isopropanol and followed by ether.

Step-b: Benzylidene Protection

Step (b) involves benzylidene protection of the compound of Formula-II to obtain a compound of Formula-III as schematically presented below;

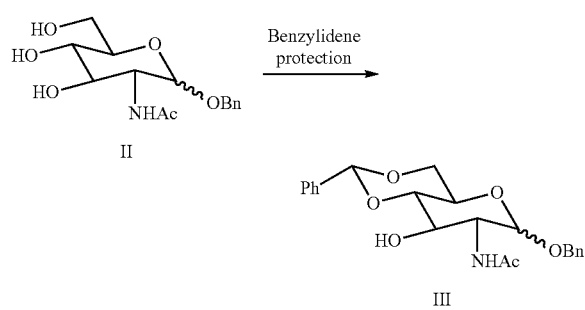

This benzyledene protection is performed by treating compound with structural Formula-II with dry benzaldehyde. The reaction can be performed in presence of metal chloride. In one embodiment the metal chloride used is zinc chloride.

The mixture is stirred at room temperature for 18 to 22 hours, preferably for 20 hours and then stirred at 35 to 45° C., preferably 40° C. for 3 to 5 hours to dissolve small amount of remaining solid followed by stirring at room temperature for 16 to 20 hours, preferably 18 hours.

After proper stirring the reaction solution is diluted with solvents, stirred and stored. In one embodiment the reaction solution is diluted with petroleum ether, absolute Ethanol and Water ($H_2O$) followed by further stirring at RT for 1-2 days and stored at 0° C. for 8 to 12 days.

Precipitate formed is washed and re-suspended in solvent. In one embodiment washing solvent is absolute EtOH and re-suspended in diethyl ether. After drying Benzyl 2-acetamido-4,6-O-benzylidene-2-deoxy-D-glucopyranoside [Compound III] is obtained. The drying can be carried out in vacuum at room temperature over phosphorous pentoxide ($P_2O_5$).

Step-c: Deacylation

Step (c) involves deacylation the compound of Formula-III to obtain a compound of Formula-IV, as schematically presented below;

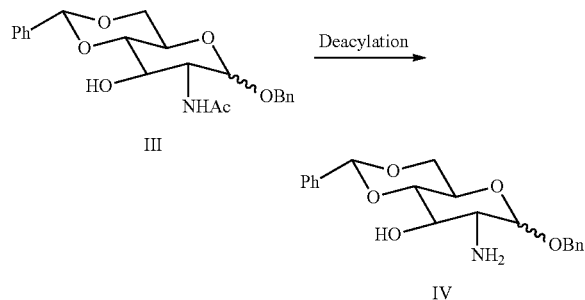

The deacylation Formula-III is carried out by treating with alcohol such as absolute ethanol in presence of a base followed by refluxing. The base may be potassium hydroxide (KOH), sodium hydroxide (NaOH), lithium hydroxide (LiOH), calcium hydroxide (CaOH) etc. In one embodiment the base used is potassium hydroxide (KOH).

The refluxing is performed under Nitrogen ($N_2$) for 8-12 hrs, preferably 10 hrs and then poured into hot water.

The suspension is stirred at low temperature (such as −5° C.) overnight for 14 to 18 hours, preferably 16 hours.

The obtained product is filtered and recrystallized. The recrystallization can be performed from solvent such as water, alcohol such ethanol, tetrahydrofuran (THF), di-isopropyl ether or mixture thereof. In one embodiment product is recrystallized from EtOH-water, followed by recrystallization from tetrahydrofuran and di-isopropyl ether (THF and i-$Pr_2O$).

Step-d: Acylation

Step (d) involves re-acylating the compound of Formula-IV with a suitable acylating agent in presence of a basic solvent, to obtain a compound of Formula-V as schematically presented below;

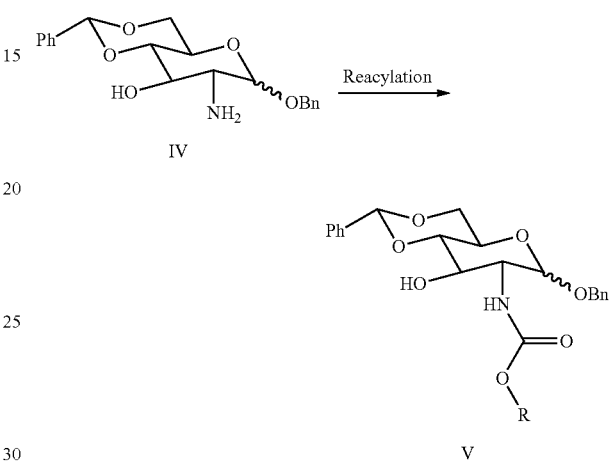

The suitable acylating agent is an organic acylating agent selected from alkyl chlofomate, alkoxy alkyl chloroformate, wherein alkyl group comprise both linear and branched structures, aryl chloroformate, and a substituted aryl group. In one preferred embodiment the organic acylating agent used in step (d) is ethyl chloroformate. The acylating agent is added slowly.

The basic solvent in acylating step (d) may be selected from dry pyridine, di-isopropyl ethyl amine, tri-ethylamine, and N,N,dimethyl amino pyridine (DMAP) or mixture thereof. In one preferred embodiment the solvent used in step (d) is dry pyridine.

In one embodiment step (d) is performed in presence of another suitable organic solvent. In one embodiment another organic solvent used is in step (d) is dichloromethane.

The acylating agent is added to the reaction mixture slowly at low temperature. In one preferred embodiment the reaction mixture is cooled to 0° C. and then ethyl chloroformate is added followed by stirring and stand overnight at room temperature.

Thus in one preferred embodiment compound of Formula IV is treated with ethyl chloroformate in presence of solvent dry pyridine in presence of distilled dichloromethane.

The reaction mixture is then diluted with a solvent, washed, filtered and dried.

In one embodiment the reaction mixture is diluted with dichloromethane and washed successively with water, saturated aqueous sodium bicarbonate and water, dried with Magnesium sulphate ($MgSO_4$), and then filtered and the filtrate is evaporated to dryness to give compound of Formula-V. Chromatographic purification can be performed such as flash chromatography on silica gel.

Step-e: O-Alkylation

Step (e) involves 0-alkylation of the compound of Formula-V by treating with L-2-chloropropanoic acid in presence of a solvent to obtain a compound of Formula-VI;

Step-f: Peptide Coupling

Step (f) involves coupling of peptide by treating the compound of Formula VI with L-alanyl-D-isoglutamine benzyl ester trifluoroacetate to obtain a compound of Formula-VII as schematically presented below;

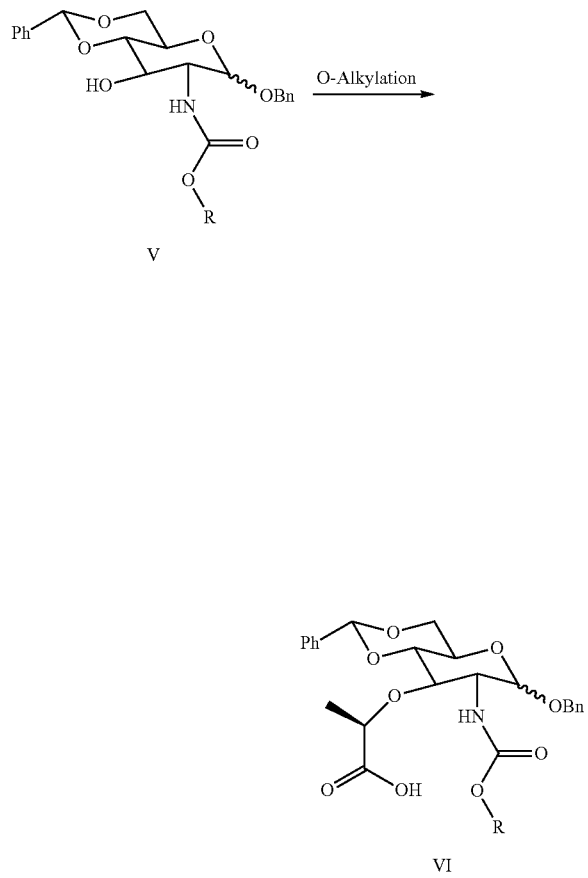

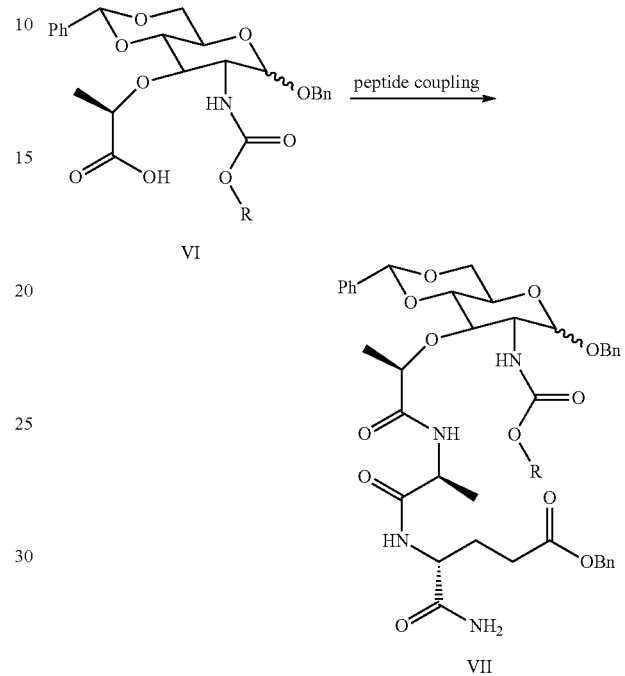

The solvent in O-Alkylating step (e) is dry dioxane. Any other similar inert high boiling solvents can also be used.

The reaction can be performed in presence of metal hydride such as sodium hydride, potassium hydride, calcium hydride etc. In one preferred embodiment the metal hydride used in step (e) is sodium hydride.

Initially the metal hydride is added at 90 to 100° C. Preferably metal hydride such as sodium hydride is added at 95° C.

After some time, such as 1 to 2 hours, the temperature is lowered to around 50 to 75° C. with stirring for overnight and then cooled with water. In one embodiment the temperature is lowered to 65° C. After further workup, extraction and drying desired compound of Formula-VI is obtained.

Aqueous mixture of compound can be extracted with solvents such as diethyl ether, chloroform or combination thereof.

The peptide compound 5 as obtained by the process shown in Scheme-A is coupled with compound of Formula-VI. Compound 5 (t-Butoxycarbonyl-L-alanyl-D-isoglutamine benzyl ester is dissolved in solvent and the resulting solution is stirred at room temperature for few minutes. Solvent is then removed and the residue is triturated with $Et_2O$ to obtain L-alanyl-D-isoglutamine benzyl ester trifluoroacetate.

The coupling takes place under standard carbodiimide coupling conditions such as in presence of 1-Ethyl-3-(-3-dimethyl amino propyl) carbodiimide (EDCI) and Hydroxybenzotriazole (HOBt).

The solvent in step (f) may be selected from trifluoroacetic acid (TFA) and tetrahydrofuran (THF) or mixture thereof. In one embodiment the solvent used in step (f) is cold trifluoroacetic acid (TFA). In another embodiment the solvent used in step (f) is THF. In another embodiment the solvent in step (f) involves both TFA and THF.

Step (f) can be performed in presence of a base. In one embodiment the base is N.N-Diisopropylethylamine (DIPEA).

The reaction mixture is stirred at RT for 12 to 18 hours, preferably 15 hours. After concentrating, the residue can be extracted with organic solvent such as chloroform and the organic layer is washed, dried and evaporated. The residue obtained can be purified on silica gel column by elution with the solvent such as chloroform, alcohols such as methanol, ethanol etc. or mixture thereof. In one embodiment chloroform-methanol mixture is used for elution.

Step-g: Deprotection

Step (g) involves de-protection of the compound of Formula-VII to obtain the desired compound as represented by Formula-VIII, as schematically presented below;

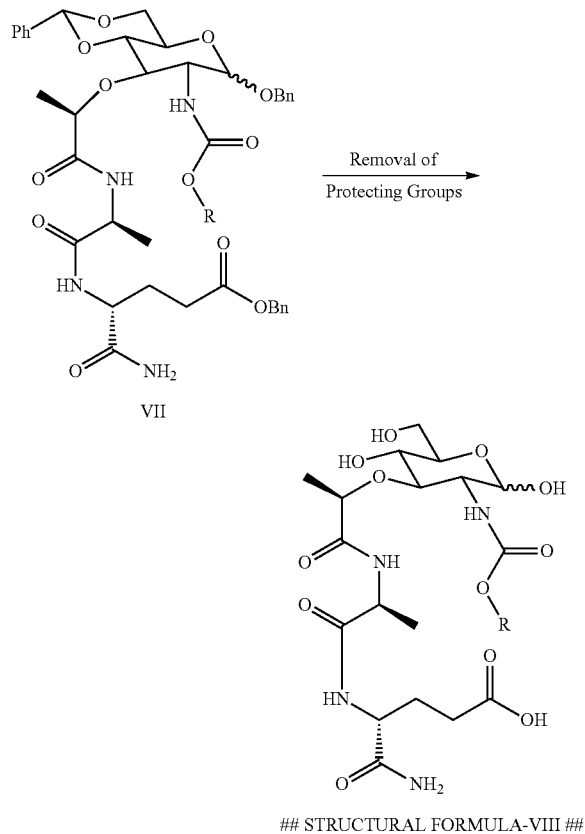

STRUCTURAL FORMULA-VIII ##

De-protection is carried out by treating compound of Formula-VII with an acid for removal of protecting groups to obtain the desired compound as represented by structural formula-VIII, wherein, R in above compounds is alkyl (both linear and branched), aryl, substituted aryl, alkoxy aryl. When R in above compounds is ethyl, the compound of Formula-VIII is MDP-ET. In one embodiment the acid used in step (g) for deprotection is glacial acetic acid.

The de-protection can be performed in presence of a catalyst. In one embodiment the catalyst used in step (g) is palladium black.

To a solution of compound of Formula-VII, dissolved in acid added with catalyst and the compound is hydrogenolyzed for 3 to 5 days in the usual way.

The catalyst is filtered off, and, after addition of water the filtrate is evaporated under diminished pressure. The residue can be column purified. In one embodiment the residue is dissolved in a small volume of acetic acid and then applied to a column of Sephadex LH-20. The purified fractions can be lyophilized. Any other suitable column can be selected.

In embodiment in the above process, R in the muramyl dipeptide derivative compound of Formula-VIII represents any alkyl (both linear and branched), aryl, substituted aryl and alkoxy alkyl group or as defined earlier in above paragraphs.

In one preferred embodiment R in the muramyl dipeptide derivative compound of Formula-VIII represents alkyl. In another preferred embodiment R is alkyl which is ethyl.

In one preferred embodiment the above described process provides the muramyl dipeptide derivative compound of Formula-VIII which is (4R)-5-amino-4-((2S)-2-((2R)-2-(((3R,4R,5S,6R)-3-((ethoxycarbonyl) amino)-2,5-dihydroxy-6-(hydroxymethyl) tetrahydro-2H-pyran-4-yl)oxy) propanamido) propanamido)-5-oxopentanoic acid (MDP-ET), when R in Formula-VIII is ethyl (C2H5) structurally as presented below.

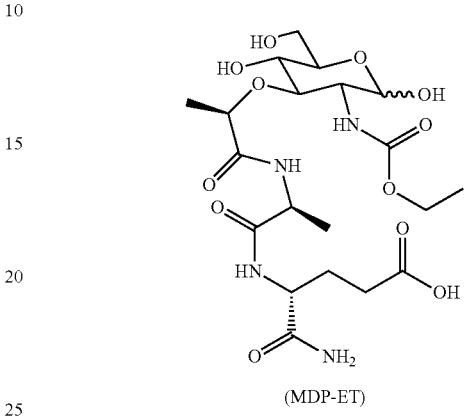

(MDP-ET)

In another aspect the invention provides process for preparation of (4R)-5-amino-4-((2S)-2-((2R)-2-(((3R,4R,5S,6R)-3-((ethoxycarbonyl)amino)-2,5-dihydroxy-6-(hydroxymethyl)tetrahydro-2H-pyran-4-yl) oxy) propanamido) propanamido)-5-oxopentanoic acid (MDP-ET) comprising the steps of:

(a) anomeric benzylation of N-acetyl D-Glucosamine (I) to obtain Benzyl 2-acetamido-2-deoxy-α-D-glucopyranoside (II);

(b) benzylidene protection of Benzyl 2-acetamido-2-deoxy-α-D-glucopyranoside (II) to obtain benzyl 2-acetamido-4,6-O-benzylidene-2-deoxy-D-glucopyranoside (III);

(c) deacylation of benzyl 2-acetamido-4,6-O-benzylidene-2-deoxy-D-glucopyranoside (III) to obtain benzyl-2-amino-4,6-O-benzylidene-2-deoxy-a-D-mannopyranoside (IV);

(d) re-acylation with an organic acylating agent ethyl chloroformate in presence of a solvent dry pyridine of benzyl-2-amino-4,6-O-benzylidene-2-deoxy-a-D-mannopyranoside (IV) to obtain ethyl ((4aR,6S,7R,8R,8aS)-6-(benzyloxy)-8-hydroxy-2-phenylhexahydropyrano[3,2-d][1,3]dioxin-7-yl) carbamate (V);

(e) o-alkylation of ethyl ((4aR,6S,7R,8R,8aS)-6-(benzyloxy)-8-hydroxy-2-phenylhexahydropyrano[3,2-d][1,3]dioxin-7-yl)carbamate (V) in presence of a solvent dry dioxane to obtain (2R)-2-(((4aR,6S,7R,8R,8aS)-6-(benzyloxy)-7-((ethoxycarbonyl)amino)-2-phenylhexahydropyrano[3,2-d][1,3]dioxin-8-yl)oxy)propanoic acid (VI);

(f) peptide coupling of (2R)-2-(((4aR,6S,7R,8R,8aS)-6-(benzyloxy)-7-((ethoxycarbonyl)amino)-2-phenylhexahydropyrano[3,2-d][1,3]dioxin-8-yl)oxy)propanoic acid (VI) with L-alanyl-D-isoglutamine benzyl ester trifluoroacetate to obtain (4R)-benzyl 5-amino-4-((2S)-2-((2R)-2-(((4aR,6S,7R,8R, 8 aS)-6-(benzyloxy)-7-((ethoxycarbonyl)amino)-2-phenylhexahydropyrano[3,2-d][1,3]dioxin-8-yl)oxy)propanamido) propanamido)-5-oxopentanoate (VII);

(g) deprotecting (4R)-benzyl 5-amino-4-((2S)-2-((2R)-2-(((4aR,6S,7R,8R, 8 aS)-6-(benzyloxy)-7-((ethoxycarbonyl)amino)-2-phenylhexahydropyrano[3,2-d][1,3]
dioxin-8-yl)oxy)propanamido)propanamido)-5-
oxopentanoate (VII) in presence of glacial acetic acid
to obtain (4R)-5-amino-4-((2S)-2-((2R)-2-(((3R,4R,
5S,6R)-3-((ethoxycarbonyl)amino)-2,5-dihydroxy-6-
(hydroxymethyl)tetrahydro-2H-pyran-4-yl)oxy)pro-
panamido)propanamido)-5-oxopentanoic acid
(Formula VIII (MDP-ET), when R is ethyl.

The above process is further explained by way of examples as provided below.

The novel MDP derivative compounds of general Formula-VIII including MDP-ET posses high potential of immuno-modulating properties.

In another aspect the present invention provides use of novel MDP derivative compounds of general Formula-VIII including MDP-ET as an adjuvant in the immunogenic preparations and vaccine formulations.

In a further aspect the invention provides a vaccine formulation comprising novel MDP derivative compounds of general Formula-VIII as an adjuvant.

In further aspects of the invention, the novel muramyl dipeptide derivative of the present invention is evaluated for its activity. The safety of the novel muramyl dipeptide derivative of the present invention is established through cytotoxicity and pyrogenecity assays.

Additionally, in further embodiments of the invention, the in-vivo immunogenecity of the novel muramyl dipeptide derivative of the present invention is shown to effectuate at least 4-fold increase in antibody titers when used as adjuvant with various vaccine antigens, thereby capable of generating both humoral and cell-mediated immune response.

The vaccine formulation comprises antigen which may be selected from a live attenuated vaccine antigen, inactivated vaccine antigen, subunit vaccine antigen, a conjugate vaccine antigen, and recombinant vaccine antigen or any combinations thereof.

Optionally, the formulation may comprise or may not comprise one or more of pharmaceutically acceptable excipients, diluents and other additive as may be required to formulate the vaccine formulation.

Non-limiting, the above vaccine formulation may be a bacterial vaccine, a viral vaccine or any potential infectious pathogens against mammals.

EXAMPLES

The novel MDP derivatives, their synthesis and novel intermediates used for synthesis and evaluation of these novel MDP derivatives as adjuvant are further explained and demonstrated by way of below non-limiting examples.

The reaction steps shown in above Scheme-A are further described in below experimental examples.

Example 1.1

SCHEME-A: Experimental Procedure for the Synthesis of L-alanyl-D-isoglutamine benzyl ester The novel MDP derivative as described and disclosed in this invention contains a L-alanyl-D-isoglutamine dipeptide entity. The L-alanyl-D-isoglutamine benzyl ester required for the final preparation of novel muramyl dipeptide compound according to the present invention was synthesized by the method as shown in above reaction Scheme-A and as described below.

Example-1.1.1

(Step-a): Preparation of (R)-2-amino-5-(benzyloxy)-5-oxopentanoic acid [Compound 2]

A mixture of D-Glutamic acid [Compound 1] (4.0 g, 27.2 mmols) and anhydrous sodium sulphate ($Na_2SO_4$ for an amount of 4.0 g) was suspended in benzyl alcohol (50 ml, 484 mmol) and Boron triflouride ($BF_3$). To this mixture, Diethyl Ether ($Et_2O$, 7.4 ml, equivalent of 54.4 mmols) was added by means of a syringe. The suspension was stirred at room temperature (RT) for 15 hrs. The mixture was diluted with absolute THF (150 ml) and filtered with the aid of charcoal. The clear filtrate was treated with Triethyl amine ($Et_3N$ for an amount of 8.2 ml, 59.2 mmols) and concentrated under vacuum until a viscous residue was formed. This viscous residue was triturated with Ethyl acetate (EtOAc for an amount of 200 ml) and the precipitated solid was isolated by suction and washed with additional solvent to get compound 2 as a white solid (6.04 g, 94%, with respect to the starting material).

Example-1.1.2

(Step-b): Preparation of (R)-5-(benzyloxy)-2-(tert-butoxy carbonyl amino)-5-oxopentanoic acid [Compound 3]

A solution of the compound 2 (6.0 g, 25.3 mmol), added with Di-tert-butyl dicarbonate ($Boc_2O$ for an amount of 6.62 g, 30.36 mmol) in dixoane and water (1:1, 40 mL) at 0° C. and the mixture was stirred overnight (16 hours). The solvent was removed under reduced pressure and the residue was diluted with water (30 mL), basified with Sodium Carbonate ($Na_2CO_3$) and washed with Ethyl Acetate (EtOAc) (3×100 mL). The aqueous layer was adjusted to pH 2-3 with a 5 M aqueous HCl solution and extracted with EtOAc (4×100 mL). The combined organic extracts were washed with brine, dried over $Na_2SO_4$ and the solvent was removed under reduced pressure to get (R)-5-(benzyloxy)-2-(tert-butoxycarbonyl)-5-oxopentanoic acid [Compound 3] (8.19 g, 96%) as a viscous colourless oil with the following NMR characteristics.

1H NMR($CDCl_3$): 7.38-7.31 (m, 5H), 5.13 (s, 1H), 2.61-2.41 (m, 2H), 2.23-1.99 (m, 2H), 1.43 (s, 9H). ESI MS:

Example-1.1.3

(Step-c): Preparation of (R)-benzyl 5-amino-4-((tert-butoxy carbonyl)amino)-5-oxopentanoate [Compound 4]

A solution of above acid Compound 3 (7.0 g, 20.8 mmol) in Tetrahydrofuran (THF for an amount of 15 mL) was prepared and added with ethyl chloroformate (2.7 mL, 28.36 mmol) and triethylamine (4.21 mL, 30.25 mmol) at 0° C. The reaction mixture was stirred at 0° C. for 0.5 hrs, then cooled to −15° C. followed by addition of methanolic solution of ammonia (25 mL, 4.0 M). Then the reaction mixture was stirred at −15° C. for another 1.5 hrs and diluted with ethyl acetate (200 mL). The organic phase was washed first with water for three times (100 mL×3) and then followed by washing with brine solution (100 mL), and dried over anhydrous sodium sulphate. The solvent was removed in vacuum and the residue was purified by flash chromatography to furnish the desired Compound 4 (6.63 g, yield 95%) as a white solid and with the following NMR characteristics.

$^1$H NMR (300 MHz, CDCl3): δ 7.35-7.30 (m, 5H), 5.12 (S, 2H), 3.70 (s, 2H), 2.58-2.42 (m, 2H), 2.31-2.19 (m, 2H) 1.43 (s, 9H); ESI MS: 337 (M$^+$).

Example-1.1.4

(Step-d): (R)-benzyl 5-amino-4-((S)-2-((tert-butoxy carbonyl)amino)propanamido)-5-oxopentanoate [Compound 5]

t-Butoxy carbonyl-D-isoglutamine benzyl ester [Compound 4] (6.5 g, 19.3 mmols) was dissolved in cold trifluoroacetic acid (20 mL) and the resultant solution was stirred at room temperature for 15 minutes. Trifluoroacetic acid was then removed and the residue was triturated with Diethyl Ether (Et$_2$O) to obtain oily D-isoglutamine benzyl ester trifluoroacetate. Oily D-isoglutamine benzyl ester trifluoroacetate was dried over Sodium hydroxide (NaOH) pellets and dissolved in THF.

Separately, t-butoxycarbonyl-L-alanine (4.012 g, 21.23 mmols) was kept in dry THF. 1-Ethyl-3-(3-dimethylaminopropyl) carbodiimide (EDCI for an amount of 4.46 g, 23.36 mmols) and Hydroxy benzotriazole (HOBt for an amount of 3.57 g, 23.36 mmols) were added to t-butoxycarbonyl-L-alanine (4.012 g, 21.23 mmols) in dry THF and stirred at Room Temperature (RT) for 30 mins. To this solution, D-isoglutamine benzyl ester trifluoroacetate (dissolved in THF) was added followed by N,N-Diisopropylethylamine (DIPEA for an amount of 7.06 ml, 40.53 mmols). The reaction was stirred at RT for 15 hrs, the solution was then concentrated and the residue extracted with EtOAc (500 ml). The EtOAc layer was washed successively with 5% Sodium Bicarbonate (NaHCO$_3$), 10% citric acid, and water (200 ml×3), then dried over Na$_2$SO$_4$ and evaporated to obtain a residue. The residue was triturated with petroleum ether to form crystals which were recrystallized from EtOAc-petroleum ether to yield compound 5 (6.37 g, 81%) as a white solid with the following NMR characteristics.

$^1$H-NMR (300 MHz, CDCl3): δ7.39-7.29 (m, 5H), 5.82 (s, 1H), 5.13-5.10 (m, 1H), 4.07 (m, 1H), 2.60-2.42 (m, 2H), 2.27-1.97 (m, 2H), 1.32 (d, 3H); Mass for C$_{15}$H$_{21}$N$_3$O$_4$: m/z Calculated 307, found 308 [M+H]$^+$.

Example 1.2

SCHEME-B

Example-1.2.1

Preparation of Benzyl 2-acetamido-2-deoxy-α-D-glucopyranoside [Compound II]

Anomeric benzylation of N-acetyl D-Glucosamine (I)

A mixture of 2-acetamido-2-deoxy-D-glucopyranose [Compound I] (15.0 g, 0.068 mol), Amberlite IR 120 [H]$^+$ ion exchange resin (15.0 g) in benzyl alcohol (125 mL) was stirred at 80° C. for 3.5 hours. The reaction mixture was filtered. The filtrate was evaporated under reduced pressure at 90° C. The residue was taken up in hot isopropanol (60 mL) and filtered. The filtrate was left to crystallize, the white crystalline solid was filtered off, washed twice with cold isopropanol (20 mL) and twice with ether (200 mL) to give benzyl 2-acetamido-2-deoxy-D-glucopyranoside [Compound II] (5.62 g, yield 27%).

Example-1.2.2

Preparation of Benzyl 2-acetamido-4,6-O-benzylidene-2-deoxy-D-glucopyranoside [Compound III]

Benzylidene Protection

Benzyl 2-acetamido-2-deoxy-D-glucopyranoside [Compound II] (4.98 g, 16.01 mol) was added to a well-stirred mixture of zinc chloride (5.0 g, 36.82 mmol) in dry benzaldehyde (16.5 ml). This mixture was stirred at room temperature for 20 hours, then stirred at 40° C. for 4 hours to dissolve a small amount of remaining solid, then stirred at room temperature for 18 hours. The well-stirred reaction solution was now diluted with petroleum ether (30 ml), absolute Ethanol (EtOH for an amount of 10 ml) and 15 ml of Water (H$_2$O). The reaction mixture was stirred for 2 days at room temperature, then stored at 0° C. for 11 days. The curdy white precipitate so formed was collected on a coarse glass frit funnel, drained thoroughly, then washed by re-suspension in absolute EtOH (approx. 50 ml). The white finely divided solid was drained thoroughly, re-suspended in diethyl ether (approx. 50 ml), re-drained thoroughly, and then dried in vacuum at room temperature over phosphorous pentoxide (P$_2$O$_5$) to get Benzyl 2-acetamido-4,6-O-benzylidene-2-deoxy-D-glucopyranoside [Compound III] (4.17 g, yield 65.4%) with the following NMR charecteristics.

$^1$HNMR(CDCl$_3$): 7.37-7.7.82 (m, 10H), 5.5 (s, 1H), 4.2-4.9 (m, 4H), 3.3-3.8 (m, 4H), 2.5 (s, 3H), ESI MS: 400 (M$^+$+1)

Example-1.2.3

Preparation of Benzyl-2-amino-4,6-O-benzylidene-2-deoxy-α-D-mannopyranoside[Compound IV]

Deacylation

A mixture of compound III (2.8 g, 6.7 mmol), 12 g Potassium Hydroxide (KOH), and 95% EtOH (40 mL) was refluxed under Nitrogen (N$_2$) for 10 hrs and then poured into hot water (150 mL). The resulting lumps of crude product were broken up. The suspension was stirred at −5° C. overnight for 16 hours. The product was filtered and was recrystallized from EtOH-water with charcoal decolorization followed by recrystallization from tetrahydrofuran and di-isopropyl ether (THF and i-Pr$_2$O). to obtain Benzyl-2-amino-4,6-O-benzylidene-2-deoxy-α-D-mannopyranoside [Compound IV] (2.3 g, yield 95%); mp: 129-131° C.; [α]$^D_{25}$+57.58 (c 2.2, DMF); IR (n in cm$^{-1}$): 3450, 3400, 750, 700; having the following NMR characteristics:

$^1$HNMR(CDCl$_3$): 7.37-7.7.82 (m, 10H), 5.5 (s, 1H), 4.9-3.3 (m, 8H), ESI MS: 358 (M$^+$+1).

Procedure for the Synthesis of (4R)-5-amino-4-((2S)-2-((2R)-2-(((3R,4R,5S,6R)-3-((ethoxycarbonyl)amino)-2,5-dihydroxy-6-(hydroxymethyl)tetrahydro-2H-pyran-4-yl)oxy)propanamido)propanamido)-5-oxopentanoic acid [Compound-VIII, when R=Ethyl]

This product was synthesized as described below.

Example-1.2.4

Preparation of ethyl((4aR,6S,7R,8R,8aS)-6-(benzyloxy)-8-hydroxy-2-phenyl hexahydropyrano[3,2-d][1,3]dioxin-7-yl)carbamate [Compound V, when R=Ethyl)]

Acylation:—

Compound IV is made to undergo re-acylation with a suitable organic acylating agent to obtain a compound with structural formula-V, wherein the said organic acylating agent is selected from alkyl chlofomate, alkoxy alkyl chloroformate, wherein alkyl group comprise both linear and branched structures, aryl chloroformate, and a substituted aryl group.

To a solution of compound IV (1.07 g, 3.0 mmol) and dry pyridine as a solvent (15 mL) in distilled dichloromethane (30 mL), cooled to 0° C., ethyl chloroformate (0.648 g, 6.0 mmol) was added slowly and the reaction mixture was stirred overnight (for 16 hours) at room temperature. Any other basic solvents such as di-sopropyl ethul amine, tri-ethylamine, N,N,dimethyl amino pyridine (DMAP) in dichloromethane instead of dry pyridine may be used. Then, the reaction mixture was diluted with dichloromethane and washed successively with water, saturated aqueous sodium bicarbonate and water, dried with Magnesium sulphate ($MgSO_4$), and then filtered and the filtrate was evaporated to dryness to give a solid which was purified by flash chromatography on silica gel, using dichloromethane-methanol as eluent, to give ethyl ((4aR,6S,7R,8R,8aS)-6-(benzyloxy)-8-hydroxy-2-phenyl hexahydropyrano[3,2-d][1,3]dioxin-7-yl) carbamate [Compound V] (1.09 g, yield 85%) with the given NMR characteristics:

$^1HNMR(CDCl_3)$: 7.2-7.5 (m, 10H), 5.6 (s, 1H), 5.4 (s, 1H), 4.7 (d, 1H), 4.6 (d, 1H), 4.4 (d, 1H), 4.2 (d, 1H), 3.7-3.9 (m, 4H), 1.4 (t, 3H), ESI MS: 430 ($M^+$)

Example-1.2.5

Preparation of (2R)-2-(((4aR,6S,7R,8R,8aS)-6-(benzyloxy)-7-((ethoxycarbonyl)amino)-2-phenyl hexahydropyrano[3,2-d][1,3]dioxin-8-yl)oxy)propanoic acid [Compound VI, when R=Ethyl)]

O-Alkylation:

To a stirred solution of compound V (0.978 g, 2.28 mmol) in dry dioxane (30 ml) as the diluent, at 95° C. sodium hydride (2.5 g) (60% oil suspension) was added. Instead of dry dioxane, any other similar inert high boiling solvents can also be used. After 1 hour, the temperature was lowered to (in others it is raised to) 65° C. and then a solution of L-2-chloropropionic acid (1.6 g) in a small volume of dioxane was added. After 1 hour, an additional 1 g of sodium hydride was added, and the reaction was continued at 65° C. with stirring and for overnight (16 hours) hours.

Then, water (150 ml) was carefully added to cool the reaction mixture. A dark-colored lower layer which developed was discarded, and the upper layer was filtered, partially concentrated, and diluted with water (100 ml). The aqueous mixture was extracted with diethyl ether, and the aqueous layer acidified to pH~3 at 0° C. and extracted with chloroform (100 ml for 3 times). The combined organic extracts were dried over anhydrous sodium sulphate and evaporated to give the desired product (2R)-2-(((4aR,6S,7R,8R,8aS)-6-(benzyloxy)-7-((ethoxycarbonyl) amino)-2-phenyl hexahydropyrano[3,2-d][1,3]dioxin-8-yl) oxy) propanoic acid [Compound VI] as a white solid (0.926 g, yield 81%) with the following NMR characteristics: $^1HNMR$ ($CDCl_3$): 7.2-7.6 (m, 10H), 5.6 (s, 1H), 5.1 (s, 1H), 4.9-3.94 (m, 7H), 3.8-3.4 (m, 4H), 1.4 (d, 2H), 1.3 (t, 3H); ESI MS: 502 ($M^+$).

Example-1.2.6

Preparation of (4R)-benzyl 5-amino-4-((2S)-2-((2R)-2-(((4aR,6S,7R,8R,8aS)-6-(benzyloxy)-7-((ethoxycarbonyl)amino)-2-phenylhexahydropyrano[3,2-d][1,3]dioxin-8-yl)oxy)propanamido)propanamido)-5-oxopentanoate [Compound VII, when R=Ethyl)]

Peptide Coupling:

Compound 5 (t-Butoxycarbonyl-L-alanyl-D-isoglutamine benzyl ester, 0.762 g, 1.87 mmols) which was obtained from Scheme-A as disclosed in Example 1.1.4 was dissolved in cold trifluoroacetic acid (10 mL) and the resulting solution was stirred at room temperature for 15 mins. Trifluoroacetic acid was then removed and the residue was triturated with $Et_2O$ to obtain L-alanyl-D-isoglutamine benzyl ester trifluoroacetate. This L-alanyl-D-isoglutamine benzyl ester trifluoroacetate was dried over NaOH pellets.

(1-Ethyl-3-(-3-dimethyl amino propyl) carbodiimide) EDCI (0.487 g, 2.55 mmols) and (Hydroxybenzotriazole) HOBt (0.390 g, 2.55 mmols) was added to compound VI (0.852 g, 1.7 mmols) in dry THF. After stirring at RT for 30 mins, L-alanyl-D-isoglutamine benzyl ester trifluoroacetate (dissolved in THF) was added followed by (N.N-Diisopropylethylamine) DIPEA (0.64 mL, 6.05 mmols). The reaction was stirred at RT for 15 hours, the solution was then concentrated and the residue extracted with chloroform ($CHCl_3$ for an amount of 50 mL). The $CHCl_3$ layer was washed successively with 5% $NaHCO_3$, 10% citric acid, and water (20 mL for three times), then dried over $Na_2SO_4$ (sodium sulphate) and evaporated. The residue obtained was purified on silica gel column by elution with the chloroform-methanol mixture to give (4R)-benzyl 5-amino-4-((2S)-2-((2R)-2-(((4aR,6S,7R,8R,8aS)-6-(benzyloxy)-7-((ethoxycarbonyl) amino)-2-phenylhexahydropyrano[3,2-d][1,3] dioxin-8-yl)oxy) propanamido) propanamido)-5-oxopentanoate [Compound VII] (1.01 g, yield 75%) with the following NMR characteristics:

$^1HNMR(CDCl_3)$: 7.5 (m, 2H), 7.2-7.4 (m, 11H), 6.9 (d, 2H) 5.5 (s, 1H), 5.2 (d, 1H), 4.9 (d, 1H), 4.7 (d, 1H), 4.5 (d, 1H), 4.4 (t, 1H), 4.2 (m 2H), 4.0 (m, 2H) 3.75 (m, 3H), 3.5 (m, H), 2.5 (s, 1H), 1.5-1.7 (m, 7H) 1.4 (t, 3H), 1.2 (t, 3H) ESI MS: 792 ($M^+$+1).

Example-1.2.7

Preparation of (4R)-5-amino-4-((2S)-2-((2R)-2-(((3R,4R,5S,6R)-3-((ethoxy carbonyl)amino)-2,5-dihydroxy-6-(hydroxymethyl)tetrahydro-2H-pyran-4-yl)oxy)propanamido)propanamido)-5-oxopentanoic acid (Formula-VIII, when R=Ethyl)

To a solution of compound VII (0.900 g, 1.13 mmol) obtained above was dissolved in glacial acetic acid (50 mL)

and was added with palladium black (90 mg) and the compound was hydrogenolyzed for 3 to 5 days in the usual way, the progress of the hydrogenolysis being monitored by thin layer chromatography. The catalyst was filtered off, and, after addition of water (30 mL), the filtrate was evaporated under diminished pressure. The residue was dissolved in a small volume of 0.1M acetic acid and then applied to a column (2.5×85 cm) of Sephadex LH-20 which was developed with the same solvent. The purified fractions corresponding to the main peak are pooled and lyophilized. The lyophilized material was rechromatographed under the same conditions, to yield compound VIII (MDP-ET) as fine, white crystals (0.326 g, 55%), with the following properties:

Melting Point (mp): 145-147° C.; $[\alpha]^{25}_D$ +53.6° (c 0.2, water);

IR (n in cm$^{-1}$): 3273, 2936, 1653, 1552, 1417, 1253, 1026;

1H-NMR (300 MHz, DMSO-d$_6$): δ 4.66 (d, J=6.421, 1H), 4.25 (m, 1H), 3.96 (m, 3H), 3.37 (q, J=6.987, 3H), 3.19-3.16 (m, 2H), 2.17 (m, 2H), 1.99 (m, 1H), 1.24 (m, 4H), 1.15 (d, J=6.409, 3H), 1.08 (t, J=6.987, 3H);

Mass for $C_{20}H_{34}N_4O_{12}$: m/z Calculated 522, found 540 $[M+NH_4]^+$.

Anal.calc. for $C_{20}H_{34}N_4O_{12}$: C, 45.97; H, 6.56; N, 10.72; O, 36.74. Found: C, 45.83; H, 6.72; N, 10.98; O, 36.81.

Example-2

Evaluation of MDP-ET Activity & Safety (In-Vitro)

Muramyl dipeptide molecules have the ability to bind to NOD2 receptors that are present on the surface of the immune cells, so as to stimulate immune response. NOD2 (Nucleotide oligomerization domain) receptor is an intracellular pattern recognition receptor (PRRs) recognizes muramyl dipeptide derivatives and stimulates cascade of signalling pathways to induce immune response. To demonstrate whether the MDP-ET synthesized in the present invention stimulates NOD2 receptors, HEK—Blue Human NOD2 reporter cell lines purchased from Invivogen, Calif., USA. These cells were prepared by co-transfection of human NOD2 gene and codon-optimized SEAP (secreted embryonic alkaline phosphatase) reporter gene into HEK 293 cells. Upon stimulation of cells with muramyl dipeptide derivative, NFkB gets activated, which intern secrets SEAP and it was measured in cell supernatant. Experimental details of this in-vitro assay are given as example 2.1.

Example 2.1

NOD2 Specific Reporter Assay

HEK—Blue Human NOD2 reporter cells (5×10$^4$/well) were plated and cultured overnight in a humidified $CO_2$ incubator at 37° C. Next day, cells were treated with various concentrations of MDP-ET, (0.001 mg/ml to 1 mg/ml) and cultured for 24-72 hrs. Supernatant was collected and treated with Quanti blue detection reagent at 37° C. for 15-30 min. Absorbance was read at 630 nm. Dose response curve generated by plotting concentration of adjuvant on X-axis and % response on the Y-axis is as shown in FIG. 1. To generate dose response curve, highest absorbance shown at tested concentration was taken as 100% response and the least absorbance was taken as 0% response. Effective concentration at 50% ($EC_{50}$) response was determined from the dose response curve. In the present invention, MDP-ET shows maximum 100% response with a high absorbance at 10 μg/ml concentration (reached plateau at this concentration in sigmoidal curve), whereas, it shows 0% response with a low absorbance at 0.01 μg/ml concentration. These results indicated $EC_{50}$ as 0.22 μg/ml (concentration at which MDP-ET showed half maximal response). In conclusion, the results obtained indicated that the novel synthesized MDP-ET in the present invention is able to stimulate NOD2 receptors, which in-turn determines further the efficiency to stimulate or enhance the immune response and act as an adjuvant.

To demonstrate whether this particular MDP-ET causes cell cytotoxicity, in-vitro cytotoxic assay was performed in J774.2A cells using MTT [3-(4,5-Dimethylthiazol-2-yl)-2,5-Diphenyltetrazolium Bromide]. Details of an assay are as explained in example 2.2.

Example 2.2

Cytotoxicity Assay

Figure 2:
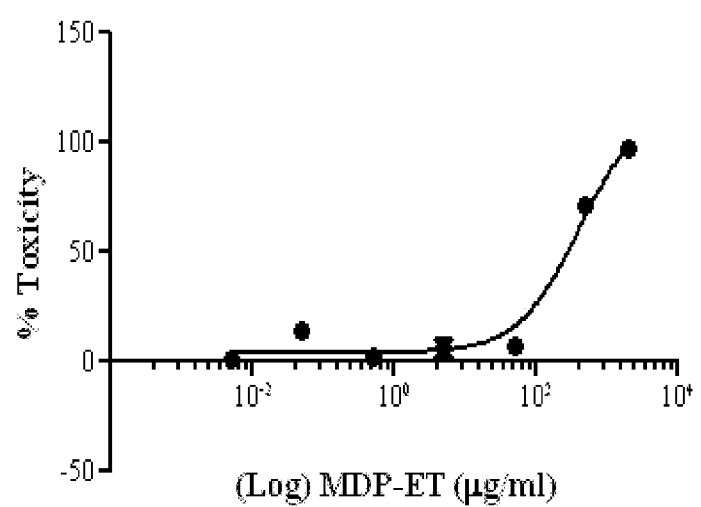
FIG. 2: The figure represents cell toxicity of MDP-ET. X-axis represents concentration in log scale and Y-axis represents % toxicity. This graph indicates $IC_{50}$ as 410 µg/ml. The concentration required to cause the cell death was found to be 410 µg/ml. Each data set point is represented as a Mean±SD, which was obtained from three independent experiments done in duplicates.

J774.2A cells (2×10$^4$/well) were plated and incubated overnight. Next day, cells were treated with various concentrations of MDP-ET (10 fold dilutions with a concentration ranging from 0.005 mg/ml to 0.5 mg/ml & 2 mg/ml) and cultured for 24 hrs. Supernatant was discarded and cells were treated with 100 μl of MTT [3-(4,5-Dimethylthiazol-2-yl)-2,5-Diphenyltetrazolium Bromide] (5 mg/ml) and incubated for 3-4 hrs until formozan crystals were formed. Later, supernatant was discarded and crystals were dissolved with DMSO for 5-10 min. Absorbance was read at 540 nm. FIG. 2 represents cell toxicity effect of MDP-ET. X-axis represents concentration in log scale and Y-axis represents % toxicity. This graph indicated $IC_{50}$ as 410 μg/ml, the concentration at which MDP-ET causes 50% cell death or toxicity effect.

Generally, pyrogenicity of any molecule can be measured by the over production of pro-inflammatory cytokines IL-1β, IL-6, and TNFα, following an activation of monocytes in-vitro, which inturn, could be an indicative of increased reactogenicity in-vivo. Hence, in the present invention, MDP-ET was tested for In-vitro pyrogenicity. Experimental details have been mentioned as below as an example 2.3. In order to determine whether the MDP-ET synthesized in the present invention, is pyrogenic or not, in-vitro pyrogen test was performed using Peripheral blood mononuclear cells (PBMCs).

Example 2.3

In-Vitro Pyrogen Test

Frozen Peripheral blood mononuclear cells (PBMCs) were revived and plated (0.5×10$^6$ cells/ml, 100 μl) in 96 well round bottom cell culture plate. Cells were supplemented with RPMI 1640 medium (Gibco Laboratories, Grand Island, N.Y.) containing fetal bovine serum (10%), glutamine (2 mM), and pencillin-streptomycin. Cells further stimulated with LPS (10 ng/ml) or endotoxin (1 EU/ml, 0.5 EU/ml, 0.25 EU/ml, 0.125 EU/ml) or MDP-ET (10 or 100 μg/ml). Cells stimulated with LPS or endotoxin was incubated for 4 hrs where as cells stimulated with MDP derivatives of the present invention kept for incubation in humidified $CO_2$ chamber at 37° C. for 24 hrs. After stimulation, cell culture supernatant was collected and cytokines (such as IL-1β, IL-6 or TNF-α) were measured by ELISA. Concentrations each cytokine produced by PBMCs in the presence of reference standard endotoxin at 0.5 EU/ml was measured in triplicates. Threshold levels were calculated for each cytokine, using the cytokine levels produced by the reference standard endotoxin at 0.5 EU/ml (Marina et al., Vaccine 30 (2012) 4859-4865).

Example 2.3.1

Determination of IL-1beta by ELISA

To determine Interleukin 1β, Enzyme Linked Immunosorbent Assay (ELISA) was performed according to the instruction manual (ebioscience, cat #88-7010). Briefly, capture antibody (cat #14-7018-67, eBioscience) was first diluted 1:250 using coating buffer and added 100 μL to each well in 96-well microplate. Plates were incubated overnight at 2-8° C. Coated plates were then washed with wash buffer (PBST). After washing, these plates were blocked using 1× assay diluent for 1 hr at room temperature followed by washing with PBST. A series of 2 fold dilutions were made from top standard ranging from 4 to 500 pg/mL, to make the standard curve. Similarly, 4 fold dilutions (1:4, 1:16 & 1:64) of cell supernatant obtained from PBMCs stimulation with MDP-ET were prepared. Aliquot (100 μL) of diluted standards or cell supernatants were added to well in duplicates and the plate was incubated at room temperature for 2 hrs. After washing the plate, 100 μL/well of detection antibody (cat #33-7016-67) diluted in 1× Assay diluent was added and incubated at room temperature for 1 hr. Later, 100 μL/well of Avidin-HRP* diluted in 1× Assay diluent was added and incubated at room temperature for 30 minutes. Finally, after washes, 100 μL of substrate solution was added to each well and incubated at RT for 15 minutes. Reaction was stopped by the addition of 50 μL of 2N $H_2SO_4$ to each well and the plate was read at 450 nm.

Example 2.3.2

Determination of IL-6 by ELISA

To determine Interleukin 6 (IL-6), Enzyme Linked Immunosorbent Assay (ELISA) was performed according to the instruction manual (ebioscience, cat #88-7066). Briefly, capture antibody (cat #14-7069-67, eBioscience) was first diluted 1:250 using coating buffer and 100 μL was added to each well in 96-well microplate. Plates were either incubated overnight at 2-8° C. Coated plates were then washed four times (350 μL/well) with 1× wash buffer previously prepared by dilution of a 20× concentrate with deionized water. After washing, plates were inverted and blotted on absorbent paper to remove any residual buffer. These plates were blocked using assay diluent (250 μL/well) for 60 minutes at room temperature followed by four times wash (350 μL/well) with 1× wash buffer. A series of 2 fold dilutions of were made from top standard ranging from 0 to 200 pg/mL, to make the standard curve. Similarly, 4 fold dilutions (1:4, 1:16 & 1:64) of cell supernatant obtained from PBMCs stimulation with MDP-ET were prepared. Aliquot (100 μL) of diluted standards or cell supernatants were added to well in duplicates and the plate was incubated at room temperature for 2 hrs. After washing the plate, 100 μL/well of detection antibody (cat #33-7068-67, eBioscience) diluted in 1× Assay diluent was added and incubated at room temperature for 1 hr. Later, 100 μL/well of Avidin-HRP* diluted in 1× Assay Diluent was added and incubated at room temperature for 30 minutes. Finally, after washes, 100 μL of Substrate Solution was added to each well and incubated at RT for 15 minutes. Reaction was stopped by the addition of 50 μL of stop solution to each well and the plate was read at 450 nm.

Example 2.3.3

Determination of TNF-alpha by ELISA

To determine Tissue Necrosis Factor-alpha (TNF-α), Enzyme Linked Immunosorbent Assay (ELISA) was performed according to the instruction manual (ebioscience, cat #88-7346). Briefly, capture antibody (cat #14-7348-67, eBioscience) was first diluted 1:250 using coating buffer and 100 μL was added to each well in 96-well microplate. Plates were either incubated overnight at 2-8° C. Coated plates were then washed four times (350 μL/well) with 1× wash buffer previously prepared by dilution of a 20× concentrate with deionized water. After washing, plates were inverted and blotted on absorbent paper to remove any residual buffer. These plates were blocked using assay diluent (250 μL/well) for 60 minutes at room temperature followed by four times wash (350 μL/well) with 1× wash buffer. A series of 2 fold dilutions of were made from top standard ranging from 4 to 500 pg/mL, to make the standard curve. Similarly, 4 fold dilutions (1:4, 1:16 & 1:64) of cell supernatant obtained from PBMCs stimulation with MDP-ET were prepared. Aliquot (100 μL) of diluted standards or cell supernatants were added to well in duplicates and the plate was incubated at room temperature for 2 hrs. After washing the plate, 100 μL/well of detection antibody (cat #33-7349-67, eBioscience) diluted in 1× Assay diluent was added and incubated at room temperature for 1 hr. Later, 100 μL/well of Avidin-HRP* diluted in 1× Assay Diluent was added and incubated at room temperature for 30 minutes. Finally, after washes, 100 μL of Substrate Solution was added to each well and incubated at RT for 15 minutes. Reaction was stopped by the addition of 50 μL of Stop Solution to each well and the plate was read at 450 nm.

Threshold levels for each cytokine were found to be as follows 370 pg/ml for IL-1β, 3110 pg/ml for IL-6 & 753 pg/ml, for TNF-α MDP-ET tested at 100 μg/ml has shown higher IL-6 levels, (above threshold value), where as IL-1β & TNF-α levels were found to be within the threshold value (data was not shown).

The compound of the present invention i.e. MDP-ET, in particular has been found to have a pronounced immuno-modulating activity, when it is used in combination with antigen(s). This activity was demonstrated using various test methods explained in more detail hereafter.

Example-3

In-Vivo Evaluation of MDP-ET for Immunogenicity

To demonstrate the ability of MDP-ET as an adjuvant and to show enhanced humoral and cell mediated response, MDP-ET was tested with two chosen antigens (recombinant Hepatitis B surface antigen, HBsAg and *Plasmodium vivax* duffy binding domain region II, PvRII), initially. However, the choice of vaccine antigens with the novel compound MDP-ET of the present invention as a vaccine adjuvant is not limited to only the vaccine antigens exemplified herein. Since, Hepatitis B vaccine is highly successful vaccine in the market with an alum as adjuvant, in the present investigation, MDP-ET was tested with HBsAg for two reasons (i) to see dose sparing effect, by using MDP-ET in place of alum, and (ii) all methods for HBsAg are very established and it is easy to screen novel adjuvants and also, it will be obvious to distinguish any observed toxicity whether caused due to the presence of the adjuvant, or alternatively, with the vaccine antigen, as HBsAg is already established and proven safe.

The vaccine antigens for combination with the vaccine adjuvant of the present invention may be formulated with other suitable vaccine antigens including but not limited to other antigens namely, ovalbumin, subunit malarial antigens comprising and all stages of life cucle, for example any form of circumsporozoite protein (CSP), rPvRII, rMsPs, rPfs25 transmission blocking antigens, rPvs25, 27, rPfF2, GLURP, liver stage antigens, inactivated rabies antigen, chikungunya virus antigen etc. The vaccine antigens of the present invention for formulation with the novel adjuvant of the present invention MDP-ET may be selected from recombinant Human papillomavirus antigen (including any and all different serotypes of HPV infection), Japanese encephalitis virus antigen, inactivated rabies antigen, hepatitis A antigen, hepatitis B antigen, hepatitis E antigen (including subunit virus like particles), ebola virus antigen any arbovirus including but not limited to zika virus, dengue vaccine antigen, diphtheria-tetanus-pertussis (either whole cell pertusis or acellular pertussis like DTaP, Tdap), *Haemophilus influenzae* type b (Hib), including any and all known form of vaccine antigens causing meningococcal infections namely *Nisseria meningitidis* A, *Nisseria meningitidis* C *Nisseria meningitidis* Y, *Nisseria meningitidis* W135, *Nisseria meningitidis* X and *Nisseria meningitidis* B. The vaccine antigens of this present invention for formulation with this novel adjuvant MDP-ET may also include *Streptococcus pneumoniae* antigens for example streptococcal *pneumoniae* serotypes 4, 6B, 9V, 14, 18C, 19F and 23F. Vaccine antigens such as *Salmonella typhi* Vi polysaccharide (either plain or conjugated), *Salmonella enteritidis*, non-typhoidal *salmonella*, *Salmonella paratyphi*, Herpes simplex virus antigen, human immunodeficiency virus antigen, cytomegalovirus antigen, H1N1 virus antigen, or tuberculosis vaccines are also included under the ambit of the present invention. Any potential live-attenuated vaccine antigen for formulation with the novel vaccine adjuvant MDP-ET of the present invention include MMR (Measles, Mumps, Rubella), chicken pox, oral polio (Sabin), influenza (the seasonal flu H1N1 virus), rotavirus and yellow fever, west nile fever vaccine. Vaccine antigens such as chikungunya virus, chandipura virus, or other forms of inactivated vaccine antigens such as inactivated polio-Salk, live attenuated sabin polio virus type I, II and III, Hepatitis A which are either heat-inactivated or chemically inactivated particles of the pathogen are also within the scope of the present invention for formulation with the novel adjuvant of the present invention. The antigens as mentioned hereinabove of the present invention may be present singly or in combinations thereof.

Example-3.1

Evaluation of an Adjuvant Effect with Ovalbumin (OVA) Antigen

Example 3.1.1

Effect of MDP-ET Analogue on Splenocyte Proliferation

Spleens were isolated from immunized mice and were processed to single cell suspension. 96 well flat bottom Micro titer plates were seeded with $1 \times 10^5$ cells/well with RPMI1640 media. Cells were treated with OVA. Con A (2 µg/mL) and LPS (10 µg/mL) or medium with a final volume of 200 µl. Plates were incubated at 37° C. with 5% $CO_2$ in an incubator. After 48 h of incubation 20 µl of Triazolyl blue Tetrazolium Bromide (MTT) solution was added to each well, incubated for next 4 h. Untransformed MTT was removed from each well by aspirating the supernatant (180 µL) and replaced with DMSO. The absorbance was read at 570 nm after 15 min.

Figure 3:
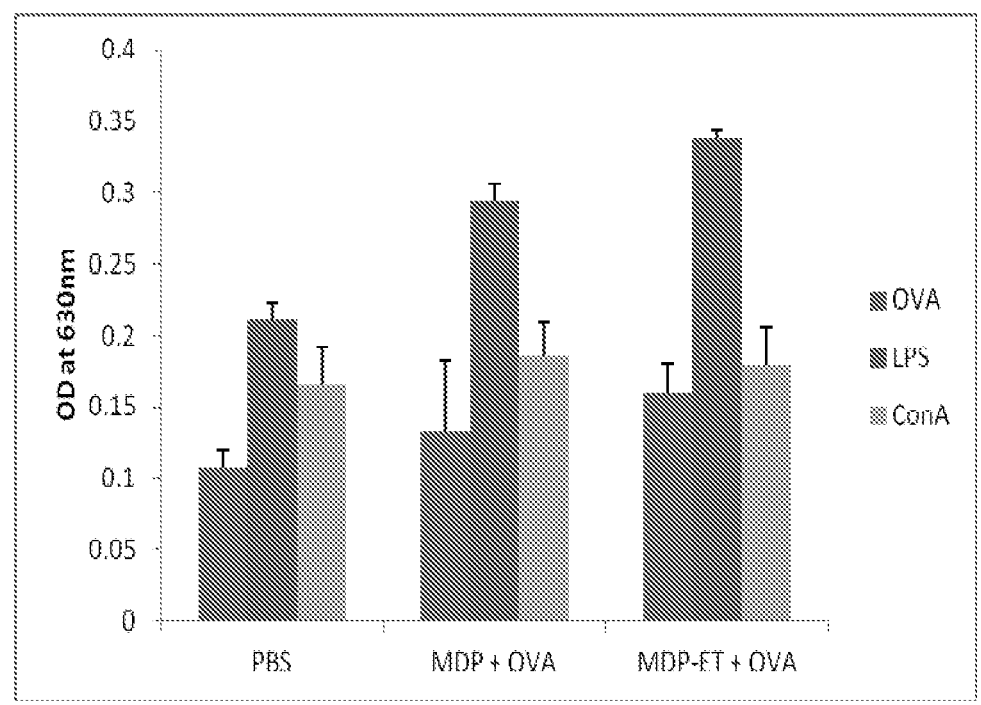
FIG. 3: Effect of MDP-ET analogue on spleenocyte proliferation.

Immunostimulating substances act through specific (antigen-dependent) T lymphocytes, B lymphocytes, and dendritic cells and also through non-specific mechanisms of action (antigen-independent) that involves granulocytes, macrophages, and NK cells. Being a secondary lymphoid organ, spleen contains a heterogeneous population of lymphocytes to examine the immunostimulant activity. However, proliferations of immune cells like T and B cells are the benchmark for immune potentiation. Mice were immunized with or without OVA or in combination with MDP and MDP-ET. Type of immune response in all treated groups was measured with LPS and Con-A splenocyte proliferation assays depicted in FIG. 3. This study revealed that the MDP-ET inducing the LPS mediated splenocyte proliferation. This is essential for B cell expansion.

Example 3.1.2

Effect of MDP-ET Analogues on OVA-Specific IgG

Male BALB/c mice were immunized subcutaneously with OVA 100 µg alone or with OVA 100 µg dissolved in saline containing analogues (7.5, 15 or 30 µg) on Days 1 and 15. Sera were collected 2 weeks after the last immunization. OVA-specific IgG antibodies in the sera were measured by an Indirect ELISA. The values are presented as log 2 titre in Table 1 as shown below.

TABLE 1

IgG titers of MDP-ET + OVA, MPD + OVA and OVA alone

| Groups | Concentration per mouse | $Log_{(2)}$ IgG Antibody Titre |
|---|---|---|
| OVA | 100 µg | 12.64 |
| MDP + OVA | 15 µg | 14.39 |
| MDP-ET + OVA | 7.5 µg | 14.89 |
| | 15 µg | 16.64 |
| | 30 µg | 17.64 |

Immune system produces required amounts of antibodies specific to pathogens/antigens. These produced antibodies neutralize the pathogens/antigens.

Real vaccine adjuvants are such molecules which can increase the production antigen specific antibodies. The above data shows IgG levels in sera collected from mice after immunization. The highest serum IgG responses were recorded for mice immunized with OVA containing MDP-ET at 15 µg and 30 µg compared to MDP+OVA group and MDP-ET has shown nearly equal antibody titer at 7.5 µg concentration.

Example-3.1.3

Effect of Analogues on Total IgG1 and IgG2a

Male BALB/c mice were immunized subcutaneously with OVA 100 µg alone or with OVA 100 µg dissolved in saline containing the MDP or MDP-ET analogues (7.5, 15 or 30 μg) on Days 1 and 15. Sera were collected 2 weeks after the last immunization. Total IgG1 and IgG2a antibodies in the sera were measured by Sandwich ELISA. The values are presented as log 2 titre in the below Table 2.

TABLE 2

IgG1 and IgG2a titers of MDP-ET + OVA, MDP + OVA and OVA alone

| Groups | Concentration per mouse | $\text{Log}_{(2)}$ Total IgG1 Antibody Titre | $\text{Log}_{(2)}$ Total IgG2a Antibody Titre |
|---|---|---|---|
| OVA | 100 μg | 14.39 | 11.89 |
| MDP + OVA | 15 μg | 18.39 | 15.64 |
| MDP-ET + OVA | 7.5 μg | 17.64 | 17.64 |
|  | 15 μg | 17.64 | 17.64 |
|  | 30 μg | 18.64 | 18.64 |

Measurement of total IgG subtypes such as IgG1 and IgG2a are useful to assess type immunity produced. In mice, IgG1 is integrated with Th2-type response, while Th1-type response is integrated with the production of IgG2a, IgG2b, and IgG3 antibodies. Antibody subclass is indispensible for complement fixation and provides protection. IgG2a and IgG2b can fix the complement stronger than IgG1. Vaccine adjuvants showing broad subclass distribution is beneficial against pathogens. The above data shows that the MDP-ET+OVA group is producing higher IgG2a response i.e., Th1 type, than MDP+OVA group in all the concentration. But, it didn't induce much significant IgG1 response i.e., Th2 type, than MDP+OVA group.

Th1:Th2 index generated by calculating the antibody titer of ova specific IgG subclasses in presence of MDP and MDP-ET were found to be 0.85 and 1 respectively. These results indicated that presence of MDP-ET might help the immune system to Th1, Th2 polarization towards Th1 response, as the Th1:Th2 index was 1.

Example 3.1.4

Effect of Analogues on Cytokines Level in Splenocytes from the OVA-Immunized Mice Male BALB/c mice were immunized subcutaneously with OVA 100 μg dissolved in saline containing MDP (15 μg) and the MDP-ET analogues (7.5, 15 or 30 μg) on Days 1 and 15. Splenocytes were prepared 2 weeks after the last immunization and cultured without and with OVA 20 μg) for 48 h Th1 (IL-2, IL-12, IFN-γ and TNF-α) and Th2 (IL 4) cytokines in the culture supernatant was measured by sandwich ELISA. The values are presented as mean±S.D. (N=3).

TABLE 3

Cytokines levels in MDP + Ova, MDP-ET + Ova immunized mice.

| Group | | IL2 (pg/ml) | IL4 (pg/ml) | IL12 (pg/ml) | IFN (pg/ml) | TNF (pg/ml) |
|---|---|---|---|---|---|---|
| MDP + OVA | Treated | 8.86 | 7.13 | 260 | 60.83 | 154.23 |
|  | Ova retreated | 9.9 | 10.05 | 290 | 141.66 | 197.15 |
| MDP-ET (7.5 μg) + OVA | Treated | 5.61 | 5.537 | 125.35 | 53.6 | 279.875 |
|  | Ova retreated | 7.12 | 8.28 | 439.3 | 76.8 | 512.12 |
| MDP-ET (15 μg) + OVA | Treated | 5.78 | 6.01 | 268 | 49.8 | 804.92 |
|  | Ova retreated | 6.93 | 13.28 | 505.8 | 50.76 | 887.27 |
| MDP-ET (30 μg) + OVA | Treated | 5.08 | 6.4 | 45.53 | 57.5 | 969.9 |
|  | Ova retreated | 7.49 | 14.76 | 49.96 | 59.6 | 1055.75 |

Cytokines secreted from the ex-vivo cultured cells would provide a support to the antibody subclass determination. Ex-vivo cultured cells with or without restimulation in presence of antigen will give the basic idea about immunological memory. Vaccine adjuvants having the ability to induce adaptive immunity with immunological memory can be identified with ex vivo cell cultures. Restimulated cultures will memorize the antigen encounter and produce significant amounts of cytokines both Th1 and Th2. Production of pro-inflammatory signals such as TNF-α is essential to combat against potent pathogens. This assay was carried out on the $28^{th}$ day of immunization schedule, spleen were collected from sacrificed mice. In each group cells were incubated with or without antigen and supernatants were measured for cytokine secretion after 48 hrs. The results revealed that, mice treated with MDP-ET+OVA at 30 μg have shown higher IL-4 and TNF-α than MDP+OVA and IL-2, IL-12 and IFN-γ responses in MDP-ET+OVA treated mice are same as MDP+OVA. Higher IL-4 secretion will activate B cell responses and it signified the higher antibody titer in previous experiments. Copious amounts of TNF-α in MDP-ET+OVA indicate delayed immune response.

Example 3.1.5

Effect of Analogues on Delayed Type Hypersensitivity (DTH) Response

Figure 4:
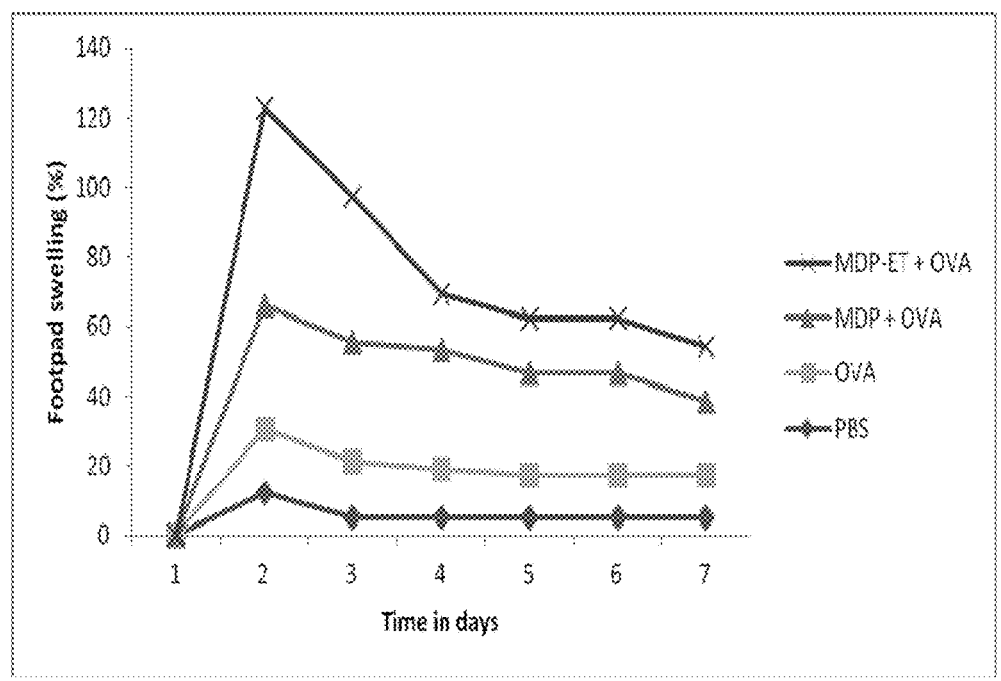
FIG. 4: Delayed type hypersensitivity responses in mice administered with MDP-ET+OVA, MDP+OVA and OVA and PBS alone.

Groups of three male BALB/c mice were immunized subcutaneously with OVA 100 μg/mice with or without 30 μg of MDP and MDP+ET analogues. After 7 days, all mice were injected subcutaneously with OVA 50 μg at both footpads. DTH responses were represented as the percentage increase of footpad swelling at the injection site represented in FIG. 4.

Delayed type hypersensitivity responses are mediated by T cells. Antigen presenting cells activates T cells secret cytokines and chemokines which stimulated the vascular endothelial cells to enhance permeability and induce phagocytes infiltration and body fluid accumulating at the site of the DTH reaction. Vaccine adjuvants enhancing the antigen effects will induce more DTH immune reaction. In the present study footpad DTH models was carried out. Usually footpad swelling reach peak at 24-48 h after antigen challenge and downhill process starts. In MDP-ET+OVA groups has shown peak at 24 h and transient decrease in footpad swelling was observed where as MDP+OVA has shown very little swelling than MDP-ET+OVA up to 7 days. DTH immune response of MDP-ET+OVA is supporting the high amount of TNF-α release for splenocyte cultures in the above experiment.

Example-3.2

Evaluation of an Adjuvant Effect with Hepatitis B Antigen

Example-3.2.1

Immunization

Female BALB/c mice (6-8 week old, n=6/group) were vaccinated intramuscularly (i.m, at two quadriceps) on Day 0 & Day 28 with vehicle control or Hepatitis B antigen (20 µg/mouse/dose/100 µl, 50 µl per quadricep) with and without MDP-ET (10 µg or 50 µg/mouse/dose/100 µl) diluted in Phosphate buffered saline. Prior to immunization, Hepatitis B surface antigen was mixed with MDP-ET, by gentle agitation (1:1 ratio), under sterile conditions. Mice were bled and euthanized on Day 42. Blood was collected & serum was isolated to evaluate analyze antigen specific total IgG antibody titer (as in example 3.1.2) and antibody subclasses (isotypes namely $IgG_1$ or $IgG_{2a}$ or $IgG_3$, as in example 3.1.3).

Example-3.2.2

Figure 5A:
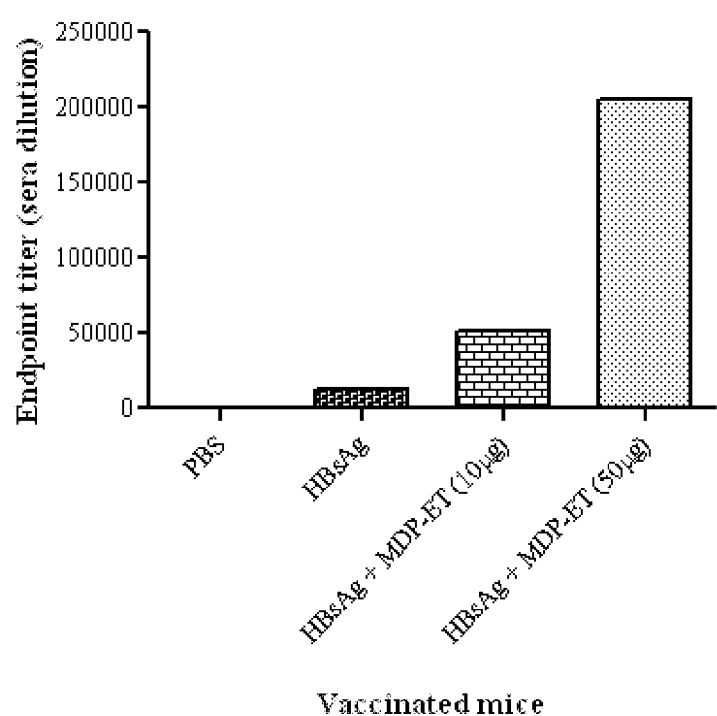
FIG. 5a: This figure shows a Hepatitis B specific endpoint titer in the presence and absence of MDP-ET. Numbers within the parenthesis indicates the concentration of MDP-ET given for vaccination along with HBsAg. Y-Axis represents sera dilution tested in ELISA.

Determination of Endpoint Titer of Antigen Specific Total IgG by ELISA-Enzyme Linked Immunosorbent Assay Serial dilutions of individual serum samples (4 dilutions ranging from 1:50 to 819200) were used to determine the endpoint titer of antigen specific total IgG antibody titer by ELISA. Details of assay protocol as described below, For analysis of antigen specific antibody titer, hepatitis B surface antigen was suspended in 50 mM carbonate bicarbonate buffer, pH 9.6 and coated at a concentration (1 µg/ml, 100 µl/well) in 96 well plates and kept at 4° C. for overnight. Next day, plates were washed with washing buffer (PBST-Phosphate buffered saline, pH 7.4 with 0.05% Tween) and blocked with blocking buffer (PBS with 1% BSA) at RT for 1-2 hr. ELISA plates were washed again with wash buffer (PBS, 0.1% Tween™20) and added serially diluted (in PBS, 0.1% BSA, 0.05% Tween™20, 0.02% sodium azide) sera from hyper immunized mice and incubated at RT for 1 hr. After incubation, wells were again washed and added Goat Anti-mouse IgG HRP conjugate antibody at a dilution of 1:5000 & incubated for 1 hr at RT. Later, wells were washed, and developed with OPD (O-phenylene diamine) as a substrate for 15 min. Reaction was stopped using $2N\ H_2SO_4$. Absorbance was read at 490 nm. Threshold (Mean+3SD) was established by taking the absorbance of negative control (PBS) group, followed by the reactive index (ratio of absorbance at a particular dilution & threshold), so as to determine end point titer. Based on this calculation, highest dilution at which reactive index value<1 was considered as endpoint antibody titer dilution. Antigen specific antibody endpoint titer in the presence & absence of MDP-ET was represented as in FIG. 5a. HBsAg specific IgG antibody titer in the presence of MDP-ET at 10 & 50 µg/mouse showed 4 fold (51200 dilution) & 8 fold (204800 dilution) increase respectively, as compared to antibody titer (12800 dilution) against HBsAg alone.

Figure 5B:
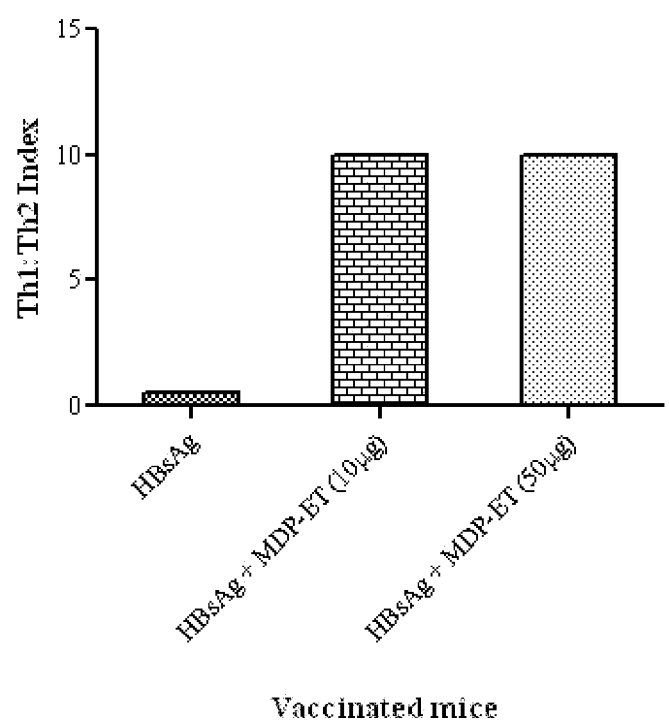
FIG. 5b: This figure represents the $T_H1$ and $T_H2$ polarization obtained in the presence and absence of MDP-ET. Numbers within the parenthesis indicates the concentration of MDP-ET given for vaccination along with HBsAg.

Similarly, MDP-ET was also tested with malarial antigen (rPvRII, *Plasmodium vivax* duffy binding protein region II, (Ref: Chitnis, C. E., and Miller, L. H. (1994) Identification of the erythrocyte binding domains of *Plasmodium vivax* and *Plasmodium knowlesi* proteins involved in erythrocyte invasion. J. Exp. Med. 180, 497-506) at 10 µg/mouse. Antigen specific antibody endpoint titer in the presence & absence of MDP-ET was represented as in FIG. 5b. rPvRII specific IgG antibody titer in the presence of MDP-ET at 10 µg/mouse showed 4 fold (51200 dilution) increase, as compared to antibody titer (12800 dilution) against rPvRII alone. rPvRII specific antibody isotypes were not tested.

It is known that, IgG subclasses produced after the immunization against given antigen, primarily determines the function of the antibody or indirectly measures the relative contribution of $T_H1$ versus $T_H2$ type cytokine induction. More specifically, production of $IgG_1$ antibodies induces $T_H2$ type cytokines, whereas, production of $IgG_{2a}$ & $IgG_3$ antibodies induces $T_H1$ type cytokines. Hence, in the present invention, we planned to determine $T_H1$, $T_H2$ polarization, after the vaccination in mice with HBsAg in the presence of MDP-ET, by analyzing IgG subclasses. In this context, in the present invention, we determined the levels of IgG isotypes ($IgG_1$, $IgG_{2a}$ & $IgG_3$), raised against HBsAg in the presence or absence of MDP-ET (at 10 & 50 µg/mouse) and calculated $T_H1$: $T_H2$ index then calculated as $([IgG_{2a}+IgG_3]/2)/(IgG_1)$. Details of assay protocol as described below as in example 3.1.3. According to such calculation, an index value<1 stands for a $T_H2$ polarization; an index value>1 stands for a $T_H1$ polarization.

Example-3.2.3

Determination of Th1:Th2 Index

Figure 5C:
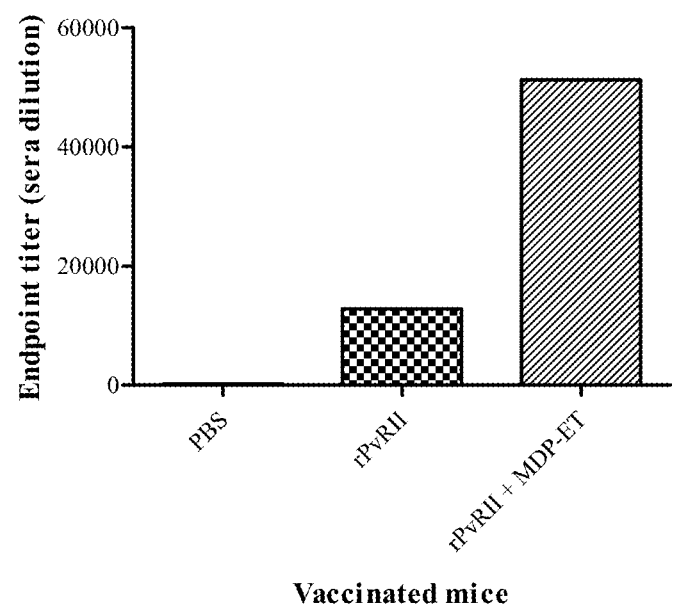
FIG. 5c: This figure shows antibody endpoint titer of rPvRII in the presence and absence of MDP-ET. Numbers within the parenthesis indicates the concentration of MDP-ET given for vaccination along with rPvRII. Y-Axis represents sera dilution tested in ELISA.

Analysis of antigen specific IgG antibody subclasses (isotypes namely $IgG_1$ or $IgG_{2a}$ or $IgG_3$) was performed as mentioned in example 3.1.2, except at one step, where goat anti-mouse $IgG_1$ or $IgG_{2a}$ or $IgG_3$ HRP was used at a dilution of 1:5000 (in place of goat anti-mouse IgG) $T_1:T_2$ index obtained at 10 & 50 µg/mouse of MDP-ET is as shown in FIG. 5c. The results indicated that HBsAg in the presence of MDP-ET also induces $T_H1$ type cytokines with $T_H1:T_H2$ index value<1 (10), whereas HBsAg alone induces $T_H2$ type cytokines with $T_H1:T_H2$ index less than 1 (0.5).

Mice vaccinated with recombinant Hepatitis B surface antigen in the presence of MDP-ET not only increased (4-8 fold, dose dependent increase) humoral response ($T_H2$) but also induced $T_H1$ type cytokines. Hence, it is concluded that the compound of the present invention possesses excellent pharmacological activity in particular adjuvant activity. Hence, MDP-ET is useful as an adjuvant in vaccine formulations. Though, MDP-ET was tested with HBsAg in the present investigation, the adjuvanated vaccine formulations comprising the present compound MDP-ET also extends to other vaccine antigens as well as already mentioned above in the preceding paragraphs.

Example-4

In-Vivo Evaluation of MDP-ET for Cytotoxicity

It has been found that the compound MDP-ET of the present invention is characterized by much less side effects and therefore tolerated upto 100 µg/rat. This particular beneficial property was evidenced by Maximum Tolerated Dose test done using rat as an animal model.

Maximum Tolerated Dose test: Wistar rats (n=6, 3M & 3F) were administered intramuscularly (i.m) with MDP-ET containing fixed adjuvant dose of 10, 50 and 100 µg/animal/ 200 µl in an ascending manner. Animals were observed daily for a period of 14 days for clinical signs & mortality. Body weight was measured daily. Food and water consumed by animals were also monitored daily for any abnormalities & Food and water intake per animal was also calculated. Body temperature was measured for every 4 hours up to 24 hrs, later once in daily up to 7 days and then followed by alternate day upto day 14. Rats were sacrificed on day 14 and organs/tissues such as site of injection, spleen, thymus, brain, lungs, Heart, liver, Kidney were collected and done macroscopic examination. No significant lesions or abnormalities found on the above mentioned organs. In this we found that there is no mortality and no significant clinical signs are observed even at tested high dose (100 µg/animal). However, weight gain is less by the animals those received high dose, compared to weight gained by the untreated animals, whereas weight gain in animals those received 10 µg & 50 µg is similar to the untreated animals. There is no temperature raise in any of the animal upto 14 days. It indicates rats are tolerable even at high dose (100 µg/animal). Blood was collected between 24-36 hrs were tested for CRP levels, after the injection. Higher (600-1000 µg/ml, normal range 200-550 µg/ml in rats) CRP levels were found at higher dose (100 µg/animal).

The above mentioned results indicated that, rats were tolerable even at tested high concentration (100 µg/animal). However, due to moderate or high levels of IL-6 levels as found in In-vitro pyrogenicity test, it can be concluded that MDP-ET may be pyrogenic at tested high concentration (100 µg/animal), which inturn correlated with high levels of CRP found immediately after giving dose. However, CRP levels were found to be normal after 14 days.

Mice vaccinated with Hepatitis B surface antigen in the presence of MDP-ET not only increased (4-8 fold, dose dependent increase) humoral response ($T_H2$) but also induced $T_H1$ type cytokines. Hence, we conclude that the present analogue 'MDP-ET' of the present invention possesses excellent pharmacological activity, in particular adjuvant activity for use as an adjuvant in vaccine formulations.

We claim:
1. A compound comprising a muramyl dipeptide of the formula:

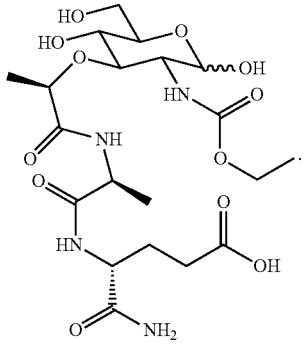 [SMILES: CCOC(=O)NC1C(O)OC(CO)C(O)C1O[C@H](C)C(=O)N[C@@H](C)C(=O)N[C@H](CCC(=O)O)C(N)=O]

2. The compound of claim 1, which comprises an IR profile characterized by IR (n in $cm^{-1}$): 3273, 2936, 1653, 1552, 1417, 1253, 1026.

3. The compound of claim 1, which comprises an NMR profile characterized by 1H-NMR (300 MHz, DMSO-$d_6$): δ 4.66 (d, =6.421, 1H), 4.25 (m, 1H), 3.96 (m, 3H), 3.37 (q, =6.987, 3H), 3.19-3.16 (m, 2H), 2.17 (m, 2H), 1.99 (m, 1H), 1.24 (m, 4H), 1.15 (d, =6.409, 3H), 1.08 (t, =6.987, 3H).

4. A vaccine formulation comprising the compound of claim 1.

5. The vaccine formulation of claim 4, further comprising an antigen selected from the group consisting of a live attenuated vaccine antigen, inactivated vaccine antigen, subunit vaccine antigen, a conjugate vaccine antigen, a recombinant vaccine antigen, and combinations thereof.

6. The vaccine formulation of claim 5, further comprising a vaccine component against an infectious pathogen.

7. The vaccine formulation of claim 6, wherein the infectious pathogen comprises bacteria, virus, or a mammalian pathogen.

* * * * *